United States Patent
Fong et al.

(10) Patent No.: US 11,215,616 B2
(45) Date of Patent: Jan. 4, 2022

(54) METHODS OF DETERMINING PATIENT POPULATIONS AMENABLE TO IMMUNOMODULATORY TREATMENT OF CANCER

(71) Applicant: The Regents of the University of California, Oakland, CA (US)

(72) Inventors: Lawrence Fong, Palo Alto, CA (US); Serena Kwek MacPhee, San Francisco, CA (US); Jera Lewis, San Francisco, CA (US)

(73) Assignee: NATIONAL INSTITUTES OF HEALTH (NIH), (DHHS), U.S. GOVERNMENT, Bethesda, MD (US)

( * ) Notice: Subject to any disclaimer, the term of this patent is extended or adjusted under 35 U.S.C. 154(b) by 333 days.

(21) Appl. No.: 15/564,704

(22) PCT Filed: Apr. 8, 2016

(86) PCT No.: PCT/US2016/026755
§ 371 (c)(1),
(2) Date: Oct. 5, 2017

(87) PCT Pub. No.: WO2016/164799
PCT Pub. Date: Oct. 13, 2016

(65) Prior Publication Data
US 2018/0074058 A1    Mar. 15, 2018

Related U.S. Application Data

(60) Provisional application No. 62/146,043, filed on Apr. 10, 2015.

(51) Int. Cl.
*A61K 39/00* (2006.01)
*G01N 33/574* (2006.01)
*G01N 33/50* (2006.01)
*C07K 16/28* (2006.01)
*G01N 33/569* (2006.01)
*C12Q 1/6886* (2018.01)

(52) U.S. Cl.
CPC ....... *G01N 33/574* (2013.01); *C07K 16/2818* (2013.01); *G01N 33/505* (2013.01); *G01N 33/56972* (2013.01); *G01N 33/5743* (2013.01); *G01N 33/57407* (2013.01); *G01N 33/57434* (2013.01); *A61K 2039/505* (2013.01); *C12Q 1/6886* (2013.01); *C12Q 2600/106* (2013.01); *C12Q 2600/158* (2013.01); *G01N 2333/70514* (2013.01); *G01N 2333/70521* (2013.01); *G01N 2333/70532* (2013.01); *G01N 2333/96436* (2013.01); *G01N 2800/52* (2013.01)

(58) Field of Classification Search
CPC .............................................. A61K 2039/505
See application file for complete search history.

(56) References Cited

U.S. PATENT DOCUMENTS

| | | | |
|---|---|---|---|
| 5,641,870 A | 6/1997 | Rinderknecht et al. |
| 5,811,097 A | 9/1998 | Allison et al. |
| 5,977,318 A | 11/1999 | Linsley et al. |
| 6,660,843 B1 | 12/2003 | Feige et al. |
| 6,682,736 B1 | 1/2004 | Hanson et al. |
| 7,109,003 B2 | 9/2006 | Hanson et al. |
| 7,442,778 B2 | 10/2008 | Gegg et al. |
| 8,258,268 B2 | 9/2012 | Wu et al. |
| 8,475,790 B2 | 7/2013 | Jure-Kunkel |
| 8,906,635 B2 | 12/2014 | Jin et al. |
| 8,993,524 B2 | 3/2015 | Bedi et al. |
| 2002/0039581 A1 | 4/2002 | Carreno et al. |
| 2005/0201994 A1 | 9/2005 | Korman et al. |
| 2013/0156774 A1 | 6/2013 | Kuchroo et al. |
| 2015/0283234 A1 | 10/2015 | Graziano et al. |

FOREIGN PATENT DOCUMENTS

| | | |
|---|---|---|
| EP | 3214175 A1 | 9/2017 |
| WO | WO-01/014424 A2 | 3/2001 |
| WO | WO 2013/126809 A1 | 8/2013 |
| WO | WO 2014/153150 A1 | 9/2014 |
| WO | WO 2015/038538 A1 | 3/2015 |

OTHER PUBLICATIONS

Gu et al. (Clin. Immunol. Sep. 2008; 128 (3): 374-810).*
Chin et al. (Chang Gung Med J. Jan.-Feb. 2008; 31 (1): 1-15).*
Jiang et al. (J. Biol. Chem. Feb. 11, 2005; 280 (6): 4656-4662).*
Riemer et al. (Mol. Immunol. 2005; 42: 1121-1124).*
Cavaco et al. (Peptide Science. 2018; 110: e23095; pp. 1-13).*
Price et al. (Mol. Cancer Ther. 2018; 17 (1 Supplement): Abstract LB-B33; DOI: 10.1158/1535-7163.TARG-17-LB-B33; pp. 1-5).*
Ramagopal et al. (Proc. Natl. Acad. Sci. USA. May 23, 2017; 114 (21): E4223-E4232).*
Callahan et al. (J. Leukoc. Biol. Jul. 2013; 94 (1): 41-53).*
Ingram et al. (Proc. Natl. Acad. Sci. USA. Apr. 10, 2018; 115 (15): 3912-7).*
Ingram et al. (Proc. Natl. Acad. Sci. USA. Apr. 10, 2018; 115 (15): 3912-3917).*
Santegoets et al. (Cancer Immunol. Immunother. Feb. 2013; 62 (2): 245-56).*
Kwek et al. (Cancer Immunol. Res. Sep. 2015; 3 (9): 1008-16).*
Jacquelot et al. (Nat. Commun. Sep. 19, 2017; 8 (1): 592; pp. 1-13).*

(Continued)

*Primary Examiner* — Stephen L Rawlings
(74) *Attorney, Agent, or Firm* — Mintz, Levin, Cohn, Ferris, Glovssky and Popeo, P.C.

(57) ABSTRACT

The disclosure provides methods of determining patient populations amenable or suitable for immunomodulatory treatment of disease such as cancer by measuring the relative or absolute levels of T-cell sub-populations correlated with disease such as cancer.

6 Claims, 14 Drawing Sheets

(56) References Cited

OTHER PUBLICATIONS

Santos-Briz et al. (Am. J. Dermatopathol. Jun. 1, 2021; 43 (6): 423-428).*
Brüggemann et al. (J. Cancer Res. Clin. Oncol. Oct. 2017; 143 (10): 1977-1984).*
European Extended Search Report, European Application No. 16777411.6, dated Jun. 29, 2018, 10 pages.
Church, S.E. et al., "Tumor-Specific CD4+ T Cells Maintain Effector and Memory Tumor-Specific CD8+ T Cells: Cellular Immune Response," European Journal of Immunology, Nov. 21, 2013, pp. 69-79, vol. 44, No. 1.
Walunas, T.L. et al., "CTLA-4 Can Function as a Negative Regulator of T Cell Activation," Immunity, 1994, pp. 405-413, vol. 1.
Krummel, M.F. et al., "CD28 and CTLA-4 Have Opposing Effects on the Response of T Cells to Stimulation," The Journal of Experimental Medicine, 1995, pp. 459-465, vol. 182.
Hodi, F.S. et al., "Improved Survival with Ipilimumab in Patients with Metastatic Melanoma," The New England Journal of Medicine, 2010, pp. 711-723, vol. 363, No. 8.
Robert, C. et al., "Ipilimumab Plus Dacarbazine for Previously Untreated Metastatic Melanoma," The New England Journal of Medicine, 2011, pp. 2517-2526, vol. 364.
Prieto, P.A. et al., "CTLA-4 Blockade with Ipilimumab: Long-Term Follow-Up of 177 Patients with Metastatic Melanoma," Clinical Cancer Research: An Official Journal of the American Association for Cancer Research, Apr. 1, 2012, pp. 2039-2047, vol. 18.
McDermott, D. et al., "Durable Benefit and the Potential for Long-Term Survival with Immunotherapy in Advanced Melanoma," Cancer Treatment Reviews, 2014, pp. 1056-4064, vol. 40.
Hodi, F.S. et al., "Ipilimumab Plus Sargramostim vs Ipilimumab Alone for Treatment of Metastatic Melanoma: a Randomized Clinical Trial," JAMA: the Journal of the American Medical Association, Nov. 5, 2014, pp. 1744-1753, vol. 312, No. 17.
Kwon E.D. et al., "Ipilimumab Versus Placebo After Radiotherapy in Patients with Metastatic Castration-Resistant Prostate Cancer that had Progressed after Docetaxel Chemotherapy (CA184-043): a Multicentre, Randomised, Double-Blind, Phase 3 Trial," The Lancet Ooncology, Jun. 2014, pp. 700-712, vol. 15.
Ku, G.Y. et al., "Single Institution Experience with Ipilimumab in Advanced Melanoma Patients in the Compassionate Use Setting: Lymphocyte Count after 2 Doses Correlates with Survival," Cancer, Apr. 1, 2010, pp. 1767-1775, vol. 116.
Wolchok, J.D. et al., "Nivolumab Plus Ipilimumab in Advanced Melanoma," The New England Journal of Medicine, 2013, pp. 122-133, vol. 369.
PCT International Search Report and Written Opinion, International Application No. PCT/US2016/026755, dated Oct. 13, 2016, 3 pp.
Barach, Yael S. et al., "T Cell Coinhibition in Prostate Cancer: New Immune Evasion Pathways and Emerging Therapeutics," Trends Mol Med. Jan. 2011; 17(I): 45-55, DOI:10.1016/j.molmed.2010.09.006.
Kwek, Serena S. et al., "Preexisting Levels of CD4 T Cells Expressing PD-1 Are Related to Overall Survival in Prostate Cancer Patients Treated with Ipilimumab." Cancer Immunol. Research, Sep. 30, 2015, Epub May 12, 2015, vol. 3, Issue 9, pp. 1008-1016; author manuscript pp. 1-32; entire documents, especially abstract.
PE-Cy5 Mouse Anti-Human CD152 (BD Bioscience) 2016 [retrieved on Jun. 1, 2016, from https://www.bdbiosciences.com/eu/applications/research/t-cell-immunology/regulator-t-cells/surface-markers/human/pe-cy5-mouse-antihuman-cd152-bni3/p/561717].
Santegoets, Saskia J.A.M. et al., "T Cell Profiling Reveals High CD4+CTLA-4+ T Cell Frequency as Dominant Predictor for Survival After Prostate GVAX/Ipilimumab Treatment," Cancer Immunol Immunother (2013) 62:245-256, DOI 10.1007/s00262-012-1330-5.
Yang, Z.Z. et al., "PD-1 Expression Defines Two Distinct T-Cell Sub-Populations in Follicular Lyphoma that Differentially Impact Patent Survival," Blood Cancer J., (2015) 5, e281; doi: 10.1038/bcj.2015.1.
Shin, S.U. et al. (1993). "Hybrid antibodies," *Int Rev Immunol* 10(2-3):177-186.

* cited by examiner

A. mCRPC Phase Ib clinical trial with ipilimumab and sargramostim

B. Metastatic melanoma Phase II clinical trial with ipilimumab and sargramostim

METHODS OF DETERMINING PATIENT POPULATIONS AMENABLE TO IMMUNOMODULATORY TREATMENT OF CANCER

CROSS REFERENCE TO RELATED APPLICATION

This application is a U.S. National Phase patent application of International Patent Application No. PCT/US16/026755, filed Apr. 8, 2016, and claims the priority benefit under 35 U.S.C. § 119(e) of Provisional U.S. Patent Application No. 62/146,043, filed Apr. 10, 2015, which are incorporated herein by reference in their entirety.

STATEMENT REGARDING FEDERALLY SPONSORED RESEARCH OR DEVELOPMENT

This invention was made with government support under grant no. RO1 CA136753 awarded by the National Institutes of Health. The federal government has certain rights in the invention.

BACKGROUND

T-cells or T lymphocytes play a central role in cell-mediated immunity. They can be distinguished from other lymphocytes by the presence of a T-cell receptor (TCR) on the cell surface. T-cells mature in the thymus (although some also mature in the tonsils). There are several types of T cells, and each type has a distinct function. The various types of T-cells include T Helper cells ($T_H$ cells), cytotoxic T-cells (CTLs), multiple sub-types of Memory T-cells, effector T cells ($T_{eff}$), regulatory T-cells ($T_{reg}$), and Natural Killer T-cells (NKT cells).

T helper cells ($T_H$ cells) assist in the maturation of B cells into plasma cells and memory B cells, as well as in the activation of cytotoxic T cells and macrophages. These $T_H$ cells, also known as CD4$^+$ T-cells, express the CD4 glycoprotein on their surfaces. Helper T-cells become activated when they are presented with peptide antigens by MHC class II molecules, which are expressed on the surface of antigen-presenting cells or APCs. Once activated, Helper T-cells divide and secrete cytokines that regulate the active immune response.

CD4 T effector cells (CD4 $T_{eff}$) are CD4$^+$ FoxP3$^-$ T cells that are not regulatory T cells and potentially have effector functions.

Cytotoxic T-lymphocyte antigen-4 (CTLA-4) is an immune checkpoint receptor expressed on T cells that mediate inhibitory immune responses in the early activation of naïve and memory T cells to maintain a balanced immune homeostasis (1) (2). CTLA-4 is found on the surface of T cells, which are involved in the cellular immune response to foreign antigen. T-cells can be activated by stimulating the CD28 receptor on the T-cell. T-cells can be inhibited by stimulating the CTLA-4 receptor, which acts as an "off" switch. CTLA-4 is a member of the immunoglobulin superfamily, which is expressed on the surface of Helper T cells and transmits an inhibitory signal to T cells. CTLA-4 is similar to the T-cell co-stimulatory protein, CD28, and both molecules bind to CD80 and CD86, also called B7-1 and B7-2 respectively, on antigen-presenting cells. In contrast to the stimulatory signal transmitted by CD28, CTLA-4 transmits an inhibitory signal to T-cells. T-cell activation through the T-cell receptor and CD28 leads to increased expression of CTLA-4, an inhibitory receptor for B7 molecules.

Programmed death 1 (PD-1) is a type I membrane protein of 268 amino acids. PD-1 appears to negatively regulate immune responses, based on PD-1 knockout mice developing lupus-like glomerulonephritis and dilated cardiomyopathy in C57BL/6 and BALB/c genetic backgrounds, respectively. T-cells stimulated by exposure to an anti-CD3 antibody that are exposed to a ligand of PD-1 (i.e., PD-L1) exhibit reduced T cell proliferation and IFN-γ secretion. These data indicate that PD-1 negatively regulates T-cell responses.

Programmed death-ligand 1 (PD-L1, CD274, B7-H1) is a type I membrane protein of 176 amino acids. PD-L1 is expressed on antigen-presenting cells (APCs), activated T cells, and a variety of tissues. PD-L1 knockout mice demonstrated increased CD4 and CD8 T cell responses including increased levels of cytokines. This data suggests that PD-L1 negatively regulates T cells and play a role in T cell tolerance.

The foregoing aspects of the immune system and the many other aspects of the immune system have been extensively studied for years as biologists and medical professionals have recognized the role played by the immune system in resisting disease and in combatting infection. Efforts to harness the considerable potential of the immune system to treat or prevent disease have led to the development of a number of biologics showing promise in the clinic. Those efforts, however, have required significant capital input and time expenditures due to care that must be taken in developing a treatment for humans, the number of failures, and the uneven response profiles of patients receiving treatment.

For all of the foregoing reasons, a need continues to exist in the art for materials and methods that yield effective immunomodulatory therapeutics, such as biologics, in an efficient manner and that more precisely target amenable or suitable patient populations for treatment or prevention.

SUMMARY

The disclosure provides methods for determining whether cancer patients are amenable or suitable for immunomodulatory treatment of the cancer by quantifying or assessing PD-1$^+$ and/or CTLA-4$^+$ and/or PD-L1$^+$ T-cell sub-types by measuring the expression of one or two or three markers, comparing the relative expression levels and determining whether the patients are amenable to such treatment based on those expression levels. The methods allow tailoring of potentially efficacious cancer treatment to precisely those patients best-situated to benefit from the costly treatments. The increased efficiency in cancer treatments will make positive contributions to cancer treatment while reducing the overall costs associated with treating the various forms of this disease.

In one aspect, the disclosure provides a method of determining that a cancer patient population is amenable to immunomodulatory inhibition of the growth of a cancer cell comprising (a) obtaining a sample from a cancer patient; (b) quantifying the percentage of PD-1$^+$ in CD4$^+$ $T_{eff}$ or total CD4$^+$ T cells in the sample; (c) assessing the percentage of PD-1$^+$ in CD4$^+$ $T_{eff}$ or total CD4$^+$ T cells from a non-cancerous subject; (d) comparing the percentage of PD-1$^+$ in CD4$^+$ $T_{eff}$ or total CD4$^+$ T cells in (b) to the percentage of PD-1$^+$ in CD4$^+$ $T_{eff}$ or total CD4$^+$ T cells in (c); and (e) determining that the cancer patient is amenable to immunomodulatory inhibition of the cancer cell when the percentage of PD-1$^+$ in CD4$^+$ $T_{eff}$ or total CD4$^+$ T cells in (b) is no greater than the percentage of PD-1$^+$ in CD4$^+$ $T_{eff}$ or total CD4+ T cells in (c). The method may further comprise contacting the sample with an anti-PD-1 antibody product and isolating the PD-1+ CD4+ T$_{eff}$ or total CD4+ T cells in the sample.

In one aspect, the disclosure provides a method of determining that a cancer patient population is amenable to immunomodulatory inhibition of the growth of a cancer cell comprising: (a) obtaining a sample from a cancer patient; (b) quantifying the percentage of CTLA-4+ in CD4+ T$_{eff}$ or total CD4+ T cells in the sample; (c) assessing the percentage of CTLA-4+ in CD4+ T$_{eff}$ or total CD4+ T cells from a non-cancerous subject; (d) comparing the percentage of CTLA-4+ in CD4+ T$_{eff}$ or total CD4+ T cells in (b) to the percentage of CTLA-4+ in CD4+ T$_{eff}$ or total CD4+ T cells in (c); and (e) determining that the cancer patient is amenable to immunomodulatory inhibition of the cancer cell when the percentage of CTLA-4+ in CD4+ T$_{eff}$ or total CD4+ T cells in (b) is greater than the percentage of CTLA-4+ in CD4+ T$_{eff}$ or total CD4+ T cells in (c). The method may further comprise contacting the sample with an anti-CTLA-4 antibody product and isolating the CTLA-4+ CD4+ T$_{eff}$ or total CD4+ T cells in the sample.

In one aspect, the disclosure provides a method of determining that a cancer patient population is amenable to immunomodulatory inhibition of the growth of a cancer cell comprising: (a) obtaining a sample from a cancer patient; (b) quantifying the percentage of PD-L1+ in CD4+ T$_{eff}$ or total CD4+ T cells in the sample; (c) assessing the percentage of PD-L1+ in CD4+ T$_{eff}$ or total CD4+ T cells from a non-cancerous subject; (d) comparing the percentage of PD-L1+ in CD4+ T$_{eff}$ or total CD4+ T cells in (b) to the percentage of PD-L1+ in CD4+ T$_{eff}$ or total CD4+ T cells in (c); and (e) determining that the cancer patient is amenable to immunomodulatory inhibition of the cancer cell when the percentage of PD-L1+ in CD4+ T$_{eff}$ or total CD4+ T cells in (b) is no greater than the percentage of PD-L1+ in CD4+ T$_{eff}$ or total CD4+ T cells in (c). The method may further comprise contacting the sample with an anti-PD-L1 antibody product and isolating the PD-L1+ CD4+ T$_{eff}$ or total CD4+ T cells in the sample.

Another aspect according to the disclosure is a method of identifying a cancer patient amenable to immunomodulatory inhibition of cancer cell growth comprising: (a) obtaining a sample from a cancer patient; (b) contacting the cancer patient sample with at least one antibody product that specifically binds a marker selected from the group consisting of PD-1, PD-L1 and CTLA-4; (c) assessing the relative level of T-cells exhibiting the marker in the CD4+ T$_{eff}$ or total CD4+ T cell population in the cancer patient sample by measuring the level of CD4+ T$_{eff}$ or total CD4+ T cells expressing the marker in the CD4+ T$_{eff}$ or total CD4+ T cell population in the cancer patient sample; (d) quantifying the relative level of T$_{eff}$ or total CD4+ T cells exhibiting the marker in the CD4+ T$_{eff}$ or total CD4+ T cell population of a sample from a non-cancerous subject by measuring the level of T$_{eff}$ or total CD4+ T cells expressing the marker in the CD4+ T$_{eff}$ or total CD4+ T cell population in the sample from the non-cancerous subject; (e) comparing the relative level of CD4+ T$_{eff}$ or total CD4+ T cells exhibiting the marker in the CD4+ T$_{eff}$ or total CD4+ T cell population of the cancer patient sample to the relative level of CD4+ T$_{eff}$ or total CD4+ T cells exhibiting the marker in the CD4+ T$_{eff}$ or total CD4+ T cell population of a sample from the non-cancerous subject; and (f) determining the cancer patient to be amenable to anti-CTLA-4 immunomodulatory inhibition of the cancer cell when the relative level of CD4+ T$_{eff}$ or total CD4+ T cells exhibiting the marker in the CD4+ T$_{eff}$ or total CD4+ T cell population in the cancer patient sample is similar or reduced relative to the level of CD4+ T$_{eff}$ or total CD4+ T cells exhibiting the marker in the CD4+ T$_{eff}$ or total CD4+ T cell population in the sample of the non-cancerous subject if the marker is PD-1 or PD-L1, or determining the cancer patient to be amenable to anti-CTLA-4 immunomodulatory inhibition of the cancer cell when the relative level of CD4+ T$_{eff}$ or total CD4+ T cells exhibiting the marker in the CD4+ T$_{eff}$ or total CD4+ T cell population in the cancer patient sample is increased relative to the level of CD4+ T$_{eff}$ or total CD4+ T cells exhibiting the marker in the CD4+ T$_{eff}$ or total CD4+ T cell population in the sample of the non-cancerous subject if the marker is CTLA-4. When referring to relative levels of CD4+ T$_{eff}$ or total CD4+ T cells being similar or reduced relative to the level of CD4+ T$_{eff}$ or total CD4+ T cells in another sample, the level in the first sample is about the same or less than the level in the second sample, i.e., the level of CD4+ T$_{eff}$ or total CD4+ T cells in the first sample is no greater than the level of CD4+ T$_{eff}$ or total CD4+ T cells in the second sample.

Another aspect is drawn to a method comprising: (a) measuring PD-1, PD-L1 and CTLA-4 expression in CD4+ T$_{eff}$ or total CD4+ T cells in a biological sample; and (b) detecting a similar or reduced level of PD-1 expression or PD-L1 expression, or an increased level of CTLA-4 expression, or any combination thereof, in the sample relative to the level in a non-cancerous subject. A related aspect of the disclosure provides a method comprising: (a) measuring PD-1, PD-L1, or CTLA-4 expression by CD4+ T$_{eff}$ or total CD4+ T cells in a biological sample that comprises T cells from a mammalian subject having cancer; and (b) detecting a similar or reduced level of PD-1-expressing CD4+ T$_{eff}$ or total CD4+ T cells, a similar or reduced level of PD-L1-expressing CD4+ T$_{eff}$ or total CD4+ T cells, or an elevated level of CTLA-4-expressing T cells in the sample relative to the level in a non-cancerous subject. Yet another related aspect of the disclosure is directed to a method comprising: (a) measuring PD-1, PD-L1 or CTLA-4 expression by CD4+ T$_{eff}$ or total CD4+ T cells in a biological sample that comprises T cells from a mammalian subject having cancer; and (b) identifying the subject as amenable to anti-CTLA-4 immunomodulatory therapy based on the measurement of the PD-1, PD-L1 or CTLA-4 expression by CD4+ T$_{eff}$ or total CD4+ T cells in the biological sample. In some embodiments of these aspects of the disclosure, PD-1 expression, or PD-L1 expression, or CTLA-4 expression is measured.

Embodiments of any of the foregoing aspects of the disclosure provide methods wherein the PD-1+ CD4+ T$_{eff}$ or total CD4+ T cells are present in the sample at a level no greater than 106 cells per microliter of sample or at a percentage no higher than 21% of the CD4+ T$_{eff}$ or total CD4+ T cells in the sample of a patient amenable to immunomodulatory inhibition of cancer cell growth. In some embodiments, the marker is CTLA-4, such as embodiments wherein the CTLA-4+ CD4+ T$_{eff}$ or total CD4+ T cells are present in the sample at a level no less than 99 cells per microliter of sample or at a percentage no less than 15.6% of the CD4+ T$_{eff}$ or total CD4+ T cells in the sample of a patient amenable to immunomodulatory inhibition of cancer cell growth. In some embodiments, the marker is PD-L1, such as embodiments wherein the PD-L1+ CD4+ T$_{eff}$ or total CD4+ T cells are present in the sample at a level no greater than 200 cells per microliter of sample or at a percentage no higher than 23.5% of the CD4+ T$_{eff}$ or total CD4+ T cells in the sample of a patient amenable to immunomodulatory inhibition of cancer cell growth.

Embodiments of any of the foregoing aspects of the disclosure provide methods wherein the sample is a tumor sample or a blood sample. By tumor sample is meant any abnormal benign or malignant growth of tissue that arises from uncontrolled cellular proliferation. A "tumor" includes one or more tumor cells and/or one or more tumor-infiltrating lymphocytes. The "blood" in a blood sample is understood to include whole blood, serum, and isolated blood cells, including peripheral blood mononuclear cells, other leukocytes, erythrocytes and platelets. Relative to tumor samples, blood samples are much easier to obtain, requiring simpler, less invasive and less risky procedures to the patient that can also be performed quicker and at reduced cost. These advantages of manipulating blood samples are apparent when the markers are potential biomarkers that have prognostic or predictive value.

Analogously, embodiments of any of the foregoing aspects of the disclosure provide methods wherein the antibody product is a polyclonal antibody, a monoclonal antibody, an antigen-binding antibody fragment thereof, a hybrid antibody, a chimeric antibody, a CDR-grafted antibody, a single-chain antibody, a single-chain variable fragment, a Fab antibody fragment, a Fab' antibody fragment, a F(ab')2 antibody fragment, a linear antibody, a bi-body, a tri-body, a diabody, a peptibody, a bispecific antibody, a bispecific T-cell engaging (BiTE) antibody, or a chimeric antibody receptor. Exemplary antibody products are an anti-PD-1 antibody product or an anti-PD-L1 antibody product or an anti-CTLA-4 antibody product. Exemplary cancer cells are an adenocarcinoma cell, a castration-resistant prostate cancer cell, a melanoma cell, a Head-and-Neck cancer cell, a lung cancer cell, a kidney cancer cell, a bladder cancer cell, a gastric cancer cell, a colorectal cancer cell, an ovarian cancer cell, a hepatocellular cancer cell, a hepatobiliary cancer cell, or a breast cancer cell, although the disclosure contemplates that any cancer cell known in the art is suitable for use in the methods. In some embodiments, the cancer cell is a an adenocarcinoma cell, a castration-resistant prostate cancer cell, a melanoma cell.

In an aspect related to each of the foregoing aspects, the disclosure provides a method as described above, further comprising (a) quantifying the granzyme B level in the $CD4^+$ $T_{eff}$ or total $CD4^+$ T cells or in the PD-$1^+$ $CD4^+$ $T_{eff}$ or PD-$1^+$ total $CD4^+$ T cells in the cancer patient sample; and (b) determining that the cancer patient is amenable to immunomodulatory inhibition of the cancer cell when the granzyme B level is elevated relative to the granzyme B level in a sample from a non-cancerous subject. In some embodiments of this aspect, the cancer patient is determined to be amenable to immunomodulatory treatment when the percentage of CTLA-$4^+$ $CD4^+$ $T_{eff}$ or CTLA-$4^+$ total $CD4^+$ T cells in $CD4^+$ $T_{eff}$ or total $CD4^+$ T cells is at least 15.6% or the number of CTLA-$4^+$ $CD4^+$ $T_{eff}$ or CTLA-$4^+$ total $CD4^+$ T cells is at least 99 cells per microliter of sample.

Another aspect related to each of the foregoing aspects of the disclosure is drawn to a method as described above, further comprising administering a therapeutically effective amount of an anti-CTLA-4 immunomodulatory agent to the subject identified as exhibiting the lower level of PD-1-expressing $CD4^+$ $T_{eff}$ or total $CD4^+$ T cells, or the lower level of PD-L1-expressing $CD4^+$ $T_{eff}$ or total $CD4^+$ T cells, or the elevated level of CTLA-4-expressing $CD4^+$ $T_{eff}$ or total $CD4^+$ T cells.

Yet another aspect of the disclosure is drawn to a use of PD-1 expression, PD-L1 expression, or CTLA-4 expression in $CD4^+$ $T_{eff}$ or total $CD4^+$ T cells in a mammalian subject having cancer for identifying a subject amenable to anti-CTLA-4 immunomodulatory therapy.

Still another aspect of the disclosure is a method of treatment of a mammalian subject having cancer comprising: (a) administering a therapeutically effective amount of an anti-CTLA-4 immunomodulatory therapy to a subject identified as amenable to anti-CTLA-4 immunomodulatory treatment based on having a lower level of PD-1-expressing $CD4^+$ $T_{eff}$ or PD-$1^+$ total $CD4^+$ T cells, or a lower level of PD-L1-expressing $CD4^+$ $T_{eff}$ or PD-$1^+$ total $CD4^+$ T cells, or an elevated level of CTLA-4-expressing $CD4^+$ $T_{eff}$ or PD-$1^+$ total $CD4^+$ T cells, or any combination thereof, as measured in a biological sample of the subject.

Another aspect of the disclosure is a cancer treatment protocol comprising: (a) measuring PD-1 or PD-L1 or CTLA-4 expression by $CD4^+$ $T_{eff}$ or total $CD4^+$ T cells in a biological sample that comprises $CD4^+$ $T_{eff}$ or PD-$1^+$ total $CD4^+$ T cells from a mammalian subject; and (b) administering a therapeutically effective amount of an anti-CTLA-4 immunomodulatory therapy to a subject identified as amenable to immunomodulatory treatment of cancer on the basis of a lower level of PD-1-expressing $CD4^+$ $T_{eff}$ or total $CD4^+$ T cells, a lower level of PD-L1-expressing $CD4^+$ $T_{eff}$ or total $CD4^+$ T cells, or an elevated level of CTLA-4-expressing $CD4^+$ $T_{eff}$ or total $CD4^+$ T cells in the sample.

The disclosure provides another aspect drawn to a method of inhibiting the growth of a cancer cell in a targeted population of cancer patients comprising (a) obtaining a sample from a cancer patient; (b) contacting the sample with an antibody product specifically binding to a T-cell marker selected from the group consisting of CTLA-4, PD-L1 and PD-1; (c) measuring the marker bound by the antibody product; (d) identifying the cancer patient as amenable to anti-CTLA-4 immunomodulatory inhibition of cancer cell growth when (i) there are more CTLA-$4^+$ $CD4^+$ $T_{eff}$ or total $CD4^+$ T cells in the $CD4^+$ $T_{eff}$ or total $CD4^+$ T cell population of the patient sample than in the $CD4^+$ $T_{eff}$ or total $CD4^+$ T cell population of a sample from a non-cancerous subject, or there are fewer PD-$1^+$ $CD4^+$ $T_{eff}$ or total $CD4^+$ T cells in the $CD4^+$ $T_{eff}$ or total $CD4^+$ T cell population of the patient sample than in the $CD4^+$ $T_{eff}$ or total $CD4^+$ T cell population of a sample from a non-cancerous subject, or there are fewer PD-L$1^+$ $CD4^+$ $T_{eff}$ or total $CD4^+$ T cells in the $CD4^+$ $T_{eff}$ or total $CD4^+$ T cell population of the patient sample than in the $CD4^+$ $T_{eff}$ or total $CD4^+$ T cell population of a sample from a non-cancerous subject; or (ii) the percentage of $CD4^+$ $T_{eff}$ or total $CD4^+$ T cells comprising the marker in the sample is at least 15.6% or the absolute quantity of $CD4^+$ $T_{eff}$ or total $CD4^+$ T cells comprising the marker in the sample is at least 99 per µl of sample, if the marker is CTLA-$4^+$, or (iii) the percentage of $CD4^+$ $T_{eff}$ or total $CD4^+$ T cells comprising the marker in the sample is no greater than 21% or the absolute quantity of $CD4^+$ $T_{eff}$ or total $CD4^+$ T cells comprising the marker in the sample is no greater than 106 per µl of sample, if the marker is PD-$1^+$, or (iv) the percentage of $CD4^+$ $T_{eff}$ or total $CD4^+$ T cells comprising the marker in the sample is no greater than 23.5% or the absolute quantity of $CD4^+$ $T_{eff}$ or total $CD4^+$ T cells comprising the marker in the sample is no greater than 200 per µl of sample, if the marker is PD-L$1^+$; and (e) administering a therapeutically effective amount of an immunomodulatory agent to the patient amenable to immunomodulatory inhibition of cancer cell growth. In some embodiments of this aspect, the sample is a tumor sample or a blood sample.

In some embodiments of this aspect of the disclosure, the antibody product is a polyclonal antibody, a monoclonal antibody, an antigen-binding antibody fragment thereof, a hybrid antibody, a chimeric antibody, a CDR-grafted antibody, a single-chain antibody, a single-chain variable fragment, a Fab antibody fragment, a Fab' antibody fragment, a F(ab')2 antibody fragment, a linear antibody, a bi-body, a tri-body, a diabody, a peptibody, a bispecific antibody, a bispecific T-cell engaging (BiTE) antibody, or a chimeric antibody receptor, such as an antibody product that is a CTLA-4-binding antibody fragment. An exemplary antibody product for use in this aspect of the disclosure is ipilimumab. Exemplary cancer cells growth-inhibited by methods of the disclosure are cells of an adenocarcinoma, a castration-resistant prostate cancer, a melanoma, a Head-and-Neck cancer, a lung cancer, a kidney cancer, a bladder cancer, a gastric cancer, a colorectal cancer, an ovarian cancer, a hepatocellular cancer, a hepatobiliary cancer, and breast cancer, although the disclosure contemplates that any cancer cell known in the art is suitable for use in the methods. In some embodiments, the cancer cell is an adenocarcinoma cell, a castration-resistant prostate cancer cell, or a melanoma cell.

Other features and advantages of the disclosure will be better understood by reference to the following detailed description, including the drawing and the examples.

DETAILED DESCRIPTION

Figure 1:
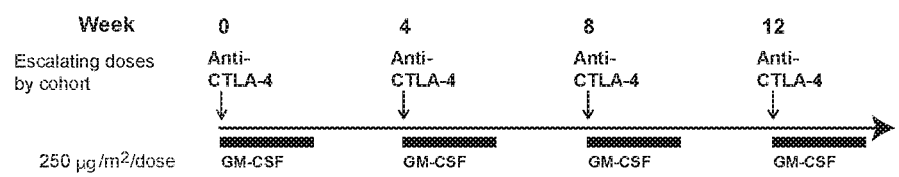
FIG. 1. Ipilimumab (anti-CTLA-4) treatment schedule. A, Metastatic castration resistant prostate cancer (mCRPC) patients were treated every 4 weeks with anti-CTLA-4 administered on day 1 of every cycle and GM-CSF administered at 250 µg/m2/dose from day 1 to day 14 daily of every cycle. Escalating doses were given to each cohort with an expansion cohort at 3 mg/kg/dose. B, Metastatic melanoma patients were treated every 3 weeks with anti-CTLA-4 administered at 10 mg/kg/dose on day 1 of every cycle and GM-CSF administered at 125 µg/m2/dose from day 1 to day 14 daily of every cycle.
Figure 1:
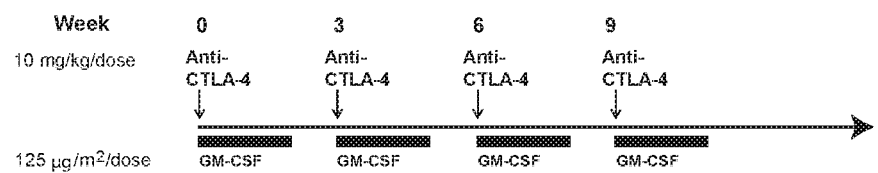

Cytotoxic T-Lymphocyte-associated antigen 4 (CTLA-4) blockade can induce tumor regression and improve survival in cancer patients. This treatment can enhance adaptive immune responses without an exogenous vaccine, but the immunologic parameters associated with improved clinical outcome in prostate cancer patients are not established. Ipilimumab is a fully humanized monoclonal antibody targeting CTLA-4 that is FDA approved for the treatment of melanoma. In two phase III studies in advanced melanoma, ipilimumab was shown to significantly prolong overall survival (OS) (3) (4). In the pivotal trial, melanoma patients were treated with ipilimumab plus gp100 (a melanoma peptide vaccine), ipilimumab alone or gp100 alone (3). The median overall survivals were 10.0, 10.1, and 6.4 months respectively. Although improvement in median overall survival was modest, a subset of patients was observed in these and other melanoma clinical trials to have durable long-term survival benefit (5) (6). Notably, long-term survival can happen without accompanying objective response. Additionally, treatment with ipilimumab plus sargramostim (GM-CSF) resulted in improved median OS and lower toxicity compared to ipilimumab alone (17.5 months versus 12.7 months) in a phase II clinical trial with unresectable melanoma (7).

A phase III clinical trial for metastatic castration resistant prostate cancer (mCRPC) treated with ipilimumab versus placebo after radiotherapy reported no significant difference in OS between the two groups (8). Median OS was 11.2 months for the ipilimumab treated group and 10.0 months for the placebo group. However, it was observed that the hazard ratio (HR) decreased over time, showing that ipilimumab associated with better survival at later time points. HR for 0-5 months was 1.46 (95% CI 1.10-1.95) and for beyond 12 months was 0.6 (95% CI 0.43-0.86). Treatment with ipilimumab also improved progression-free survival compared to placebo (median 4.0 versus 3.1 months; HR 0.70; p-value less than 0.001). Post hoc analysis showed that patients who have no visceral metastases benefited more from ipilimumab treatment than those that do have visceral metastases (HR 1.64; p-value=0.0056).

Disclosed herein is an up-dated long-term follow-up of a phase Ib dose escalation trial in patients with metastatic, castration resistant prostate cancer (mCRPC) was performed combining ipilimumab (anti-CTLA-4) and sargramostim (GM-CSF). Patients were followed clinically for response and overall survival, and for immunomodulation of circulating T cells. Of the 42 mCRPC enrolled patients, five patients had PSA declines of at least 50% with associated radiographic responses in two patients from the groups treated with at least 3 mg/kg of ipilimumab. Long-term follow-up demonstrated that 16 patients (38%) had overall survival of greater than 30 months, of whom four patients had PSA declines of at least 50% or objective responses. The combination of GM-CSF and ipilimumab can induce prolonged survival in a subset of patients who did not have PSA or objective responses. Clinical responses were both immediate and delayed. Two patients were still alive with overall survivals of 4.8 and 7 years as of censored date on Oct. 21, 2014. One of these patients had a continued PSA response without additional therapy.

Disclosed herein are the clinical results of a phase II trial in patients with metastatic melanoma was performed combining ipilimumab (anti-CTLA-4) and sargramostim (GM-CSF). Of the 22 metastatic melanoma patients, one patient received only 1 cycle of ipilimumab and sargramostim and was not included in subsequent analysis. Of the 21 remaining patients, one patient had complete response (CR), 6 patients had partial response (PR), 1 patient had stable disease (SD), and 13 patients had progressive disease (PD). These clinical responses were found to associate with overall survival. As of censored date on Feb. 12, 2015, 10 patients were still alive.

Immune subsets in peripheral blood mononuclear cells (PBMC) were evaluated for 23 out of 42 mCRPC patients whom were treated with ipilimumab at 3 mg/kg/dose or greater and sargramostim at 250 µg/m²/dose. Immune subsets were examined in PBMC from baseline, after cycle 1 and after cycle 2 of treatment with flow cytometry. As the number of clinical responses observed were low, comparison of immune subsets were made between patients who had overall survival greater than the median (23.6 months) for the group (long-term survivors, LTS, OS range: 25.4 months-99.7 months) (n=11)) versus patients who had overall survival less than the median for the group (short-term survivors, STS, OS range: 1.9 months-22.4 months) (n=12)).

Immune subsets in PBMC were evaluated for all 21 metastatic melanoma patients who were treated with ipilimumab at 10 mg/kg/dose and sargramostim at 125 µg/m²/dose. Immune subsets were examined in PBMC from baseline, after cycle 1 and after cycle 2 of treatment with flow cytometry. As the number of patients who were alive is almost half of all the patients, comparison of immune subsets were made between patients with complete response, partial response and stable disease (responders, R, n=8) versus patients who had progressive disease (non-responder, NR, n=13)

Disclosed herein are the results that pre-treatment clinical characteristics of patients where applicable, such as age, LDH levels, Eastern Cooperative Oncology group (ECOG) performance status, Gleason score of tumors, metastatic stages, prior treatments, and subsequent therapies after leaving clinical trial did not relate with survival for mCRPC patients and clinical responses for metastatic prostate cancer patients.

It has been shown that the absolute lymphocyte counts after two ipilimumab treatments correlate significantly with clinical benefit and OS in a clinical trial for melanoma. Disclosed herein are the results that for our clinical trials, the levels of absolute lymphocyte counts of patients at pre-treatment or after cycle 1 and cycle 2 of treatment did not relate with survival for mCRPC patients and clinical responses for metastatic prostate cancer patients.

Disclosed herein are the results that lower pre-treatment levels of PD-1$^+$ CD4 T$_{eff}$ cells and higher pre-treatment levels of CTLA-4$^+$ CD4 T cells, were each significantly associated with better overall survival for mCRPC patients. The levels of these same immune subsets examined after cycle 1 and cycle 2 did not relate with survival. The levels of the parent subsets, total CD4 T cells, CD4 T$_{eff}$ cells, and CD8 T cells did not relate with survival at pre-treatment or after cycle 1 and cycle 2 of treatment.

Disclosed herein are the results that lower pre-treatment levels of PD-L1$^+$ CD4 T cells and PD-1$^+$ CD4 T$_{eff}$ cells were significantly associated with clinical responses for metastatic melanoma patients. The levels of PD-L1$^+$ CD4 T cells and PD-1$^+$ CD4 T$_{eff}$ cells also relate with survival after cycle 2 but not after cycle 1 of treatment. The levels of total CD4 T cells also relate with responses at pre-treatment, after cycle 1 and cycle 2 of treatment.

Disclosed herein are the results that mCRPC patients with poorer survival have significantly higher pre-treatment levels of PD-1$^+$ CD4 T$_{eff}$ cells compared to cancer-free controls, whereas patients with better survival have similar pre-treatment levels of PD-1$^+$ CD4 T$_{eff}$ cells compared to cancer-free controls.

Disclosed herein are the results that mCRPC patients with poorer survival have similar or slightly higher pre-treatment levels of CTLA-4$^+$ CD4 T cells compared to cancer-free controls, whereas patients with better survival have significantly higher pre-treatment levels of CTLA-4$^+$ CD4 T cells compared to cancer-free controls.

Disclosed herein are the results that metastatic melanoma patients with progressive disease have significantly higher pre-treatment levels of PD-L1$^+$ CD4 T cells and PD-1$^+$ CD4 T$_{eff}$ cells compared to cancer-free controls, whereas patients with clinical responses or stable disease have similar pre-treatment levels of PD-L1$^+$ CD4 T cells and PD-1$^+$ CD4 T$_{eff}$ cells compared to cancer-free controls.

Disclosed herein are the results that a proportion of these PD-1$^+$ CD4 T$_{eff}$ cells express granzyme B without activation and IFNγ upon PMA/ionomycin activation, which is consistent with an effector T cell phenotype.

Without wishing to be bound by theory, a potential explanation for the association of PD-1$^+$ and PD-L1$^+$ CD4 T cells with poorer survival is that CTLA-4 blockade with ipilimumab treatment removes inhibition on T cells that express CTLA-4, but tolerance to tumor antigens maintained by PD-1$^+$ or PD-L1$^+$ CD4 T cells persists and results in poorer survival. In addition it may also explain the increased effectiveness of combined CTLA-4 and PD-1 blockade therapies (10), especially as CTLA-4 blockade also increased the levels of PD-1+ CD4 effector T cells during treatment. It is expected that low PD-1 and/or low PD-L1 but high CTLA-4 levels in CD4 T cells will be useful as biomarkers for improved survival following CTLA-4 blockade immunotherapy and it is expected that high PD-1 but low CTLA-4 levels will characterize patients suitable for combination immunotherapy with anti-PD-1 and anti-CTLA-4 immunotherapeutics.

The following examples illustrate embodiments of the disclosure.

Example 1

Materials and Methods
Clinical Trial

For mCRPC, the results for the lower dose levels up to 3 mg/kg/dose for this phase Ib trial have been previously described (13). Briefly, patients had histologically proven metastatic castration resistant adenocarcinoma of the prostate with progression as defined by the PSA Working Group Consensus Criteria (14). Patients had received no prior steroids, chemotherapy or immunotherapy treatment. Patients received escalating doses of ipilimumab (Bristol-Myers Squibb) with a fixed dose of sargramostim (Sanofi). The initial design included dose escalation of ipilimumab from 0.5 mg/kg to 3 mg/kg (0.5, 1.5, and 3) every 4 weeks for 4 doses (13). The study was subsequently modified to include 5 and 10 mg/kg dose levels, as well as an expansion cohort of 6 patients at 3 mg/kg/dose (cohort 5A) (Table 1). Sargramostim at 250 µg/m2/dose on days 1-14 of 28 days cycles was administered subcutaneously and continued until disease progression or grade 3 or 4 treatment-related toxicity.

For mCRPC, the primary endpoint of safety was graded according to National Cancer Institute (NCI) Common Terminology Criteria for Adverse Events version 3.0. Dose-limiting toxicity (DLT) included grade 3 or 4 treatment-related toxicity but excluded grade 3 immune-related adverse events (unless ocular) that did not require the use of steroids. Exploratory endpoints included T-cell activation, objective tumor responses (decrease in tumor size and/or lesions) as defined by Response Evaluation Criteria in Solid Tumors (RECIST) (15), and PSA declines of ≥50% in PSA levels confirmed 4 weeks later defined by the PSA Working Group Consensus Criteria. Progression is defined as a 50% rise in PSA above the nadir or back to baseline, whichever is lower, on at least two consecutive measurements at least two weeks apart; or the appearance of one or more new lesions occurring more than one month after the initiation of therapy. Bone scans (and CT scans if abnormal) were repeated every 12 weeks and at the time of PSA progression. Best PSA decline was the maximum percentage (%) decline from initial PSA levels before treatment. Overall survival (OS) was calculated from date of first treatment to date of death (n=40) or censor date of trial on Oct. 21, 2014 (n=2).

For metastatic melanoma, inclusion criteria were histologically confirmed, surgically incurable or unresectable, Stage III or IV metastatic melanoma. Patients must have had disease progression following 1 systemic therapy for metastatic disease, a minimum of 1 measurable lesion according to irRC criteria, ECOG performance status of 0-2, and LDH ≤4× upper limit of normal (ULN). Patients had no uncontrolled brain metastasis, no history of autoimmune disease, and no prior immunotherapy treatments. Patients were treated with treated with 4 courses of GM-CSF and ipilimumab administered every 3 weeks. GM-CSF will be administered subcutaneously daily in a dose of 125 µg/m$^2$ beginning on day 1 to day 14 of each 21-day cycle and ipilimumab will be administered intravenously in a dose of 10 mg/kg on day 1 of each cycle. After the initial 3 months (4 cycles) of treatment, GM-CSF administration continued for 4 additional cycles on the same schedule and dose without ipilimumab for 14 days every 21 days until month 6. Maintenance therapy began at month 6 and consisted of ipilimumab in the same dose combined with 14 days of GM-CSF. Administration of this combination was repeated every 3 months for up to 2 years or until disease progression, whichever occurred first.

For metastatic melanoma, primary end point is disease control rate at 24 weeks. Secondary endpoints are assessment of immune activation, duration of disease control, overall survival, objective response rate using the immune related Response Criteria (irRC) (11), time to objective response, duration of objective response (CR or PR), and safety of the combination as defined by the NCI CTCAE criteria Version 4.0. Disease assessments will be performed using CT scans of the chest, abdomen, and pelvis and MRI scan of the brain at screening and every 3 months. OS was calculated from date of first treatment to date of death (n=11) or censor date of trial on Feb. 12, 2015 (n=10).

Flow Cytometry

Staining for flow cytometry was carried out on cryopreserved peripheral blood mononuclear cells (PBMC). In addition to study participants, PBMC were also obtained from men undergoing prostate cancer screening without a subsequent diagnosis of cancer (cancer-free male controls). Cell surface staining was performed in FACS buffer for 30 min at 4° C. Intracellular FoxP3, CTLA-4, and Ki67 staining was performed using the FoxP3 fix/perm buffer set (Biolegend, Inc., 421403) according to the manufacturers' protocol. CD49b, granzyme B, and Lag-3 were stained using the intracellular fixation and permeabilization buffer set (eBioscience, Inc., 88-8824). Intracellular IFNγ and IL-4 were stained suing the Foxp3 staining buffer set (eBioscience, Inc., 00-5523) after PBMC were activated with 50 ng/ml PMA and 1 µg/ml ionomycin for four hours at 37° C. in the presence of 5 µg/ml of Brefeldin A for the last two hours of activation. The following anti-human antibodies were used: (A700)-CD3 (Biolegend, Inc., 300324), (BV570)-CD4 (Biolegend, Inc., 300533), (PerCP/Cy5.5)-CD8 (Biolegend, Inc., 301032), (BV650)-CD25 (Biolegend, Inc., 302633), (FITC)-CD49b (Biolegend, Inc., 359306), (A647)-CD127 (Biolegend, Inc., 351318), (PE)-CTLA-4 (Biolegend, Inc., 349906), (A488)-FoxP3 (Biolegend, Inc., 320112), (PE)-Granzyme B (BD Biosciences, 561142), (BV650)-IFNγ (Biolegend, Inc., 502537), (A647)-IL-4 (Biolegend, Inc., 500712), (APC)-Lag-3 (eBioscience, Inc., 3DS223H), (BV421)-PD-1 (Biolegend, Inc., 329920), and (PE-Cy7)-PD-L1 (BD Biosciences, 558017). Stained cells were analyzed with an LSRII (BD Biosciences) flow cytometer. Data analysis was performed with Flowjo software (Treestar). Percentage (%) of positive cells was gated based on appropriate isotype control. Absolute count for each immune subset is calculated by multiplying the percentage of each subset with the preceding parent subset and with the absolute lymphocyte count quantitated on the day of blood drawn for that sample.

Statistical Analysis

Distributions of percentage of paired immune subsets at pre-treatment (week 0) were compared with cycle 1 (week 4 for mCRPC patients; week 3 for metastatic melanoma patients) or with cycle 2 (week 8 for mCRPC patients; week 6 for metastatic melanoma patients) using Wilcoxon matched-pairs signed rank test using Prism (GraphPad) software. The number of patients with PBMC at the various time points differed based on availability.

Distributions of categorical patient characteristics such as ECOG status, Gleason score, prior radical prostatectomy, prior radiation, subsequent therapies, and clinical responses for mCRPC patients, sex, tumor stage, presence of immune adverse related events, prior therapy, and prior systemic therapy for metastatic melanoma patients were compared using Fisher's exact test with Prism (Graphpad) software.

Distributions of continuous patient characteristics where applicable, such as age, baseline PSA levels, lactate dehydrogenase (LDH) levels, months on study, percentage or absolute counts of immune subsets between long-term survivors (LTS) and short-term survivors (STS), and percentage or absolute counts of immune subsets between responders (R) and non-responders (NR). Percentage of immune subsets between cancer-free male controls and LTS or STS or R or NR were similarly compared using Mann-Whitney U-test.

Comparison of overall survival of cancer patients divided into two groups based on cutoff levels of immune subsets were carried out by plotting Kaplan-Meier curves for each group and carrying out log-rank test.

Statistical significance was declared based on alpha level of 0.05 with Bonferroni correction to adjust for multiple testing as needed. Due to the small sample size, all significant outcomes should be considered as hypothesis generating and confirmation with a larger sample size are needed.

Example 2

Patient Characteristics

TABLE 1

Patient Characteristics for mCRPC

| N = 42 | Median (range) |
|---|---|
| Age (years) | 72.5 (52-82) |
| ECOG PS (n) | |
| 0 | 31 |
| 1 | 11 |
| Gleason score | |
| ≤6 | 8 |
| 7 | 11 |
| ≥8 | 21 |
| Baseline PSA (ng/mL) | 37.5 (6.7-435) |
| LDH (U/L) | 172 (136-557) |
| Alkaline phosphatase (U/L) | 92 (28-1725) |
| Metastases | |
| Bone | 25 |
| Soft tissue | 5 |
| Both | 12 |

TABLE 2

Patient Characteristics for metastatic melanoma

| N = 22 | Percentage (range) |
|---|---|
| Age, median (range), years | 65 (41-85) |
| Sex | |
| Men | 12 (54.5) |
| Women | 10 (45.5) |

TABLE 2-continued

Patient Characteristics for metastatic melanoma

| N = 22 | Percentage (range) |
|---|---|
| Metastatic Stage | |
| Unresectable III | 1 (4.55) |
| M1a | 1 (4.55) |
| M1b | 5 (22.7) |
| M1c | 15 (68.2) |
| Sites of Metastasis | |
| Lymph Nodes | 14 (63.6) |
| Lung | 14 (63.6) |
| Liver | 10 (45.5) |
| Bone | 7 (31.8) |
| Subcutaneous tissue | 6 (27.3) |
| CNS | 4 (18.2) |
| Skin | 3 (13.6) |
| Adrenal | 3 (13.6) |
| Intestine | 1 (4.55) |
| Spleen | 1 (4.55) |
| Retroperitoneum | 1 (4.55) |
| Received prior systemic therapy | |
| No | 15 (68.2) |
| Yes | 7 (31.8) |
| Prior Therapy | |
| Radiation | 9 (40.9) |
| Systemic, Chemo | 4 (18.2) |
| Adjuvant | 3 (13.6) |
| Systemic, Non-Chemo | 2 (9.1) |
| Localized | 1 (4.5) |

Example 3

Clinical Outcomes

Figure 2:
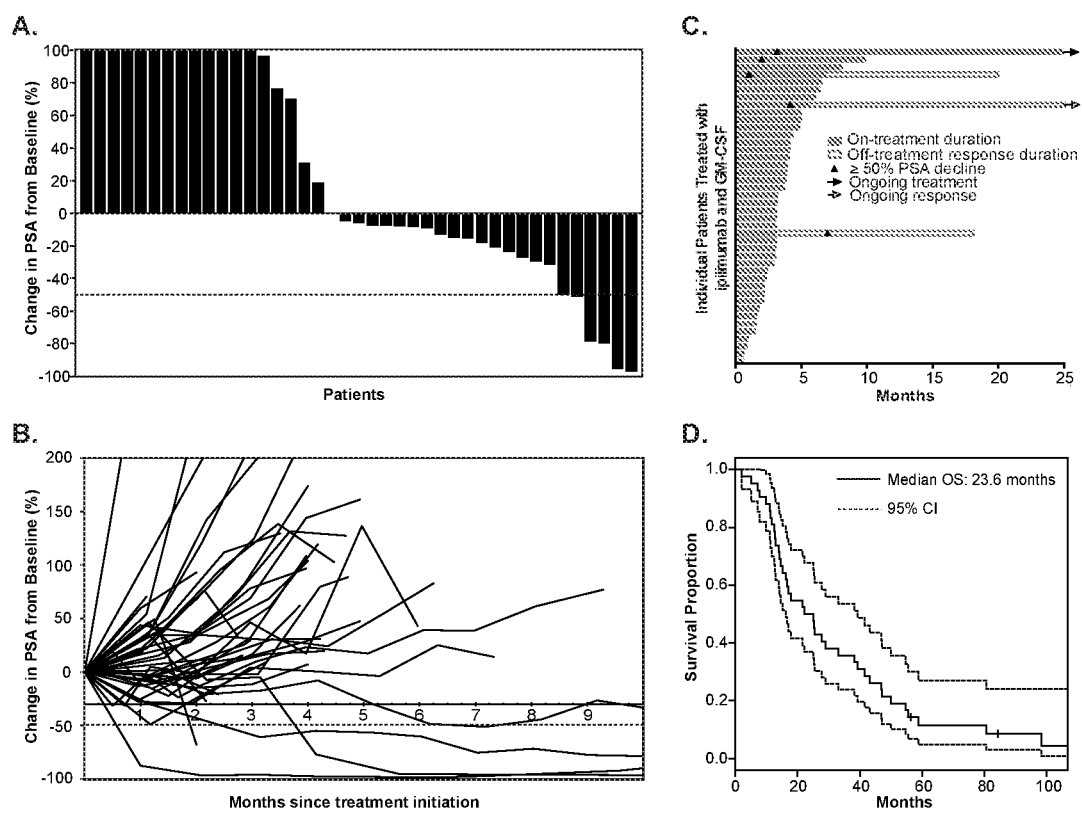
FIG. 2. Clinical outcomes of 42 metastatic castration resistant prostate cancer (mCRPC) patients in a Phase Ib ipilimumab (anti-CTLA-4) and GM-CSF clinical trial. A, Waterfall plot of the maximum percentage change in PSA from baseline of each patient until nadir or off study. Dashed line shows 50% decline in PSA. B, Spider plot shows change in PSA with time from baseline of each patient until nadir or off study. Dashed line shows 50% decline in PSA. C, Graph showing the duration of study treatment, duration of response, time to disease progression, and time to at least 50% decline in PSA for each patient. D, Overall survival curve for all patients as of analysis on the censor date. Dotted lines below and above the survival curve (solid line) show lower and upper 95% confidence intervals (CI) respectively. Vertical tick marks indicate OS of patients who were still alive as of the censor date.

A waterfall plot of nadir PSA values (FIG. 2A) demonstrates that 23 out of 42 patients (54%) had some decline in PSA. Five of 42 patients (11.9%) experienced a 50% or greater decline in PSA (Table 1). The median time to PSA nadir was 5.9 weeks (range 1.9-39.1 weeks) for patients with any PSA decline and 15.9 weeks (range 11.9-39.1 weeks) for patients with at least a 50% PSA decline (FIG. 2B). Objective tumor response and at least a 50% PSA decline was not observed in cohorts treated at less than 3 mg/kg/dose level. Three out of 12 patients treated at 3 mg/kg/dose experienced at least a 50% PSA decline, of whom two had objective responses with regression of liver metastasis in one patient and bone metastasis in another (cohort 5). One patient in the expansion cohort at 3 mg/kg experienced a 49% decline (cohort 5A). In the cohort treated at 5 mg/kg/dose, none of 6 patients demonstrated at least a 50% PSA decline or objective tumor response. Of the 6 patients treated at the 10 mg/kg, two had at least a 50% PSA decline. No accompanying objective tumor response was seen.

As of censor date of the trial, all patients had come off study. One patient came off treatment by patient's choice. 13 patients came off treatment for PSA progression prior to the first set of scans, 16 patients came off treatment with PSA progression following the first set of scans, 6 patients came off treatment for tumor progression by scans, and 6 patients came off treatment for immune-related adverse toxicities. However, two patients from the 3 mg/kg/dose group whom came off treatment due to immune-related toxicities demonstrated durable responses with their PSA levels remaining less than 50% of their pre-treatment levels for 19 and 85 months after being off treatment without any new treatment (FIG. 2C). One patient from the 5 mg/kg/dose group came off treatment due to an initial disease progression, but a delayed response was observed with his PSA decline attaining 50% at 7 months without any new treatment.

As this is a Phase Ib study, survival analysis was not specified in the protocol. As immunotherapies can induce improvements in overall survival without conventional progression, survival analysis was carried out post-hoc. The median OS for all the patients (n=42) is 23.6 months (95% confidence limits {CI}={116.2, 39.3}) (FIG. 2D).

TABLE 3

Clinical Responses for mCRPC

| Dose Level[a] | ≥50% PSA Response (Best decline %) | Objective Response[b] | TTP[c] (months) | Median Overall Survival (months) |
|---|---|---|---|---|
| 1 (0.5 mg/kg x 4) | 0/3 | 0/3 | | 25 |
| 2 (1.5 mg/kg x 1, 0.5 mg/kg x 3) | 0/7 | 0/7 | | 26 |
| 3 (1.5 mg/kg x 4) | 0/5 | 0/5 | | 28 |
| 4 (3 mg/kg x 1, 1.5 mg/kg x 3) | 0/3 | 0/3 | | 12 |
| 5 (3 mg/kg x 4) | 3/6 (79, 95, 97) | 2/6 | 20, 25.75, 89.25 | 56 |
| 6 (5 mg/kg x 4) | 0/6 | 0/6 | | 13 |
| 7 (10 mg/kg x 4) | 2/6 (50, 80) | 0/6 | 9.75, 18 | 19 |
| 5A (3 mg/kg x 4) | 0/6 | 0/6 | | 20 |
| Cumulative | 5/42 | 2/42 | 20 (median) | 23.6 |

[a]Dosage of ipilimumab and the number of doses are given in brackets ( );
[b]Objective tumor response defined by RECIST;
[c]TTP is time to progression calculated from the time of initial response.

Figure 3:
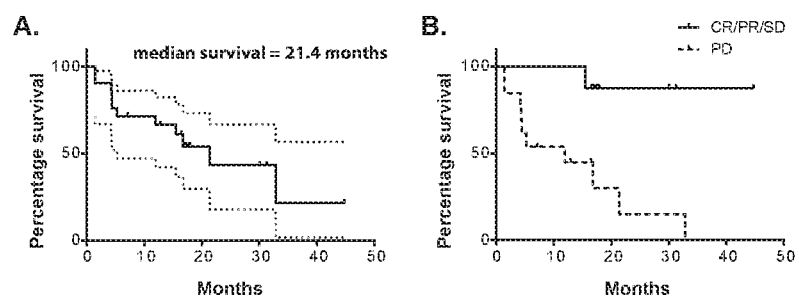
FIG. 3. Clinical outcomes of 21 metastatic melanoma patients in a Phase II ipilimumab (anti-CTLA-4) and GM-CSF clinical trial. A, Overall survival curve for all patients as of analysis on the censor date. Dotted lines below and above the survival curve (solid line) show lower and upper 95% confidence intervals (CI) respectively. Vertical tick marks indicate OS of patients who were still alive as of the censor date. B, Kaplan-Meier plots of treated melanoma patients separated by presence of complete response (CR) plus partial response (PR) plus stable disease (SD) compared to patients with progressive disease (PD). Sum of patients with CR, PR or SD are hence denoted as responders (R) and sum of patients with PD are hence denoted as non-responders (NR).

Clinical outcomes for metastatic melanoma: Out of 21 patients who had received at least 2 cycles of treatment, 1 patient had CR, 6 patients had PR, 1 patient had SD, and 13 patients had PD. The median OS for all the treated patients (n=22) was 21.4 months (FIG. 3A). Overall survival associated significantly with clinical responses (CR+PR) plus SD (FIG. 3B) (p-value=0.005).

Example 4

Toxicity

Consistent with the known toxicity profile of ipilimumab, toxicity was primarily immune in nature.

TABLE 4

Adverse events for mCRPC

| Dose Level | All adverse events[a] | Dose-Limiting Toxicities |
|---|---|---|
| 1 | 1/3<br>grade 1: nausea (1) | 0/3 |
| 2 | 1/7<br>grade 3: CVA (1) | 1/7<br>grade 3: CVA |
| 3 | 2/5<br>grade 3: fatigue (1), rash (1) | 1/5<br>grade 3: rash requiring steroids |
| 4 | 0/3 | 0/3 |
| 5 | 4/6<br>grade 2: muscle spasms (1)<br>grade 3: angina (1), temporal arteritis (1), diarrhea (1), panhypopituitarism (1)<br>grade 4: CVA (1) | 1/6<br>grade 4: CVA |
| 6 | 5/6<br>grade 1: fatigue (1), muscle spasms (1), diarrhea (2)<br>grade 2: wheezing (1), hot flashes (1), fatigue (1), pruritus (2), rash (3)<br>grade 3: fatigue (1), atrial fibrillation (1)<br>grade 5: PE (1) | 1/6<br>grade 5: PE |
| 7 | 6/6<br>grade 1: diarrhea (1), rash (1)<br>grade 2: vomiting (1), dehydration (1), pruritus (3), fatigue (1), erythema (1), adrenal insufficiency (2)<br>grade 3: fatigue (2), diarrhea (2), rash (3)<br>grade 4: elevated troponin (1) | 1/6<br>grade 3: rash requiring steroids |
| 5A[b] | 4/4<br>grade 1: increased LFT (1)<br>grade 2: adrenal insufficiency (1), pneumonitis (1)<br>grade 3: atrial fibrillation (1), DVT (1), diarrhea (1)<br>grade 4: fatigue (1) | 1/4<br>grade 3: diarrhea requiring steroids |

[a]Immune-related adverse events are in bold. The fraction of patients with any adverse event is presented per cohort. The number of patients with each adverse event is listed in brackets ( ). As a patient might have experienced more than one adverse event, the sum of all adverse events may be greater than the number of patients in each cohort;
[b]Information for adverse events was available only for four out of six patients in this cohort;
CVA, cerebrovascular accidents; DVT, deep venous thrombosis; LFT, liver function test; PE, pulmonary embolism.

TABLE 5

Adverse events for metastatic melanoma

| Toxicity | % Grades 1-2 | % Grades 3-4 |
|---|---|---|
| Fatigue | 50 | 6.25 |
| Injection Site Reaction | 43.75 | 6.25 |
| Infusion Reaction | 12.5 | 6.25 |
| Fever | 12.5 | 0 |
| Flu-like symptoms | 6.25 | 0 |
| Irritability | 6.25 | 0 |
| Flushing | 6.25 | 0 |
| Gastrointestinal | 50 | 37.5 |
| Diarrhea | 18.75 | 12.5 |
| Nausea | 31.25 | 0 |
| Colitis | 0 | 18.75 |
| Colon Perforation | 0 | 6.25 |
| Skin and Subcutaneous | 81.25 | 6.25 |
| Rash | 31.25 | 6.25 |
| Pruritis | 31.25 | 0 |
| Urticaria | 12.5 | 0 |
| Hyperhidrosis | 6.25 | 0 |
| Anorexia | 37.5 | 6.25 |
| Investigational | 25 | 6.25 |
| Weight loss | 12.5 | 0 |
| Decreased ACTH | 0 | 6.25 |
| Increased AST | 6.25 | 0 |
| Increased ALT | 6.25 | 0 |
| Nervous System | 25 | 0 |
| Headache | 12.5 | 0 |
| Tremor | 6.25 | 0 |
| Dysgeusia | 6.25 | 0 |
| Cardiac | 12.5 | 6.25 |
| Palpitations | 6.25 | 0 |
| Atrial fibrillation | 0 | 6.25 |
| Pericarditis | 6.25 | 0 |
| Endocrine | 6.25 | 6.25 |
| Hyperthyroidism | 6.25 | 6.25 |
| Musculoskeletal | 12.5 | 0 |
| Myalgias | 6.25 | 0 |
| Arthalgias | 6.25 | 0 |
| Infection | 6.25 | 0 |
| Phayrngitis | 6.25 | 0 |

Example 5

Patients' Baseline Characteristics Did not Relate with Survival for mCRPC Patients or Clinical Responses for Metastatic Melanoma Patients.

Figure 11:
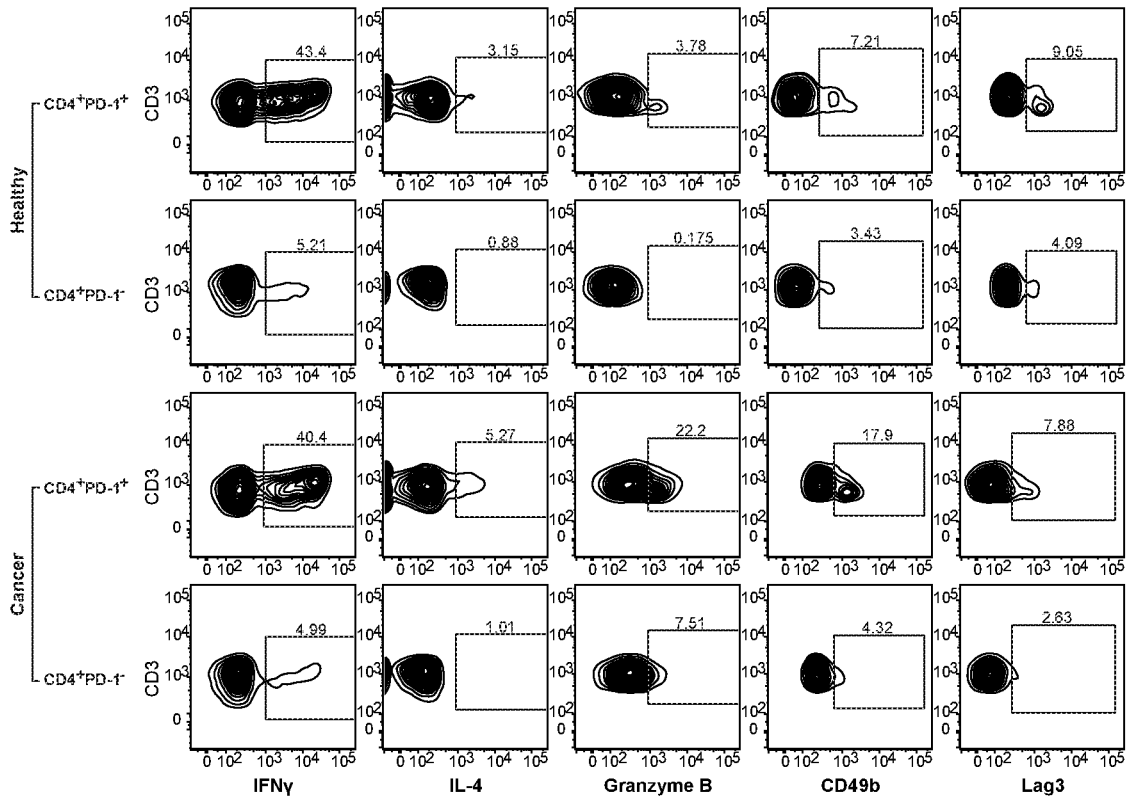
FIG. 11. A, Cytokine expression and surface markers of PD-1$^+$ and PD-1$^-$ CD4 T cells. Representative flow cytometry diagrams showing percentages of IFNγ, IL-4, granzyme B, CD49b, and Lag-3 expression in PD-1$^+$ and PD-1$^-$ CD4 T cells for one out of three healthy donors and one out of six mCRPC patients. Pre-treatment PBMC from cancer patients were used. B, Cytokine expressions and surface markers of PD-1$^+$ and PD-1$^-$ CD8 T cells. Representative flow cytometry diagrams showing percentages of IFNγ, IL-4, granzyme B, CD49b, and Lag-3 expression in PD-1$^+$ and PD-1$^-$ CD8 T cells for one out of three healthy donors and one out of six mCRPC patients. Pre-treatment PBMC from cancer patients were used. For IFNγ and IL-4 staining, PBMC were stimulated with PMA and ionomycin for 4 hours in culture at 37° C. with Brefeldin A added at the last 2 hours of incubation. For granzyme B, CD49b, and Lag-3 staining, unstimulated PBMC were used.
Figure 11:
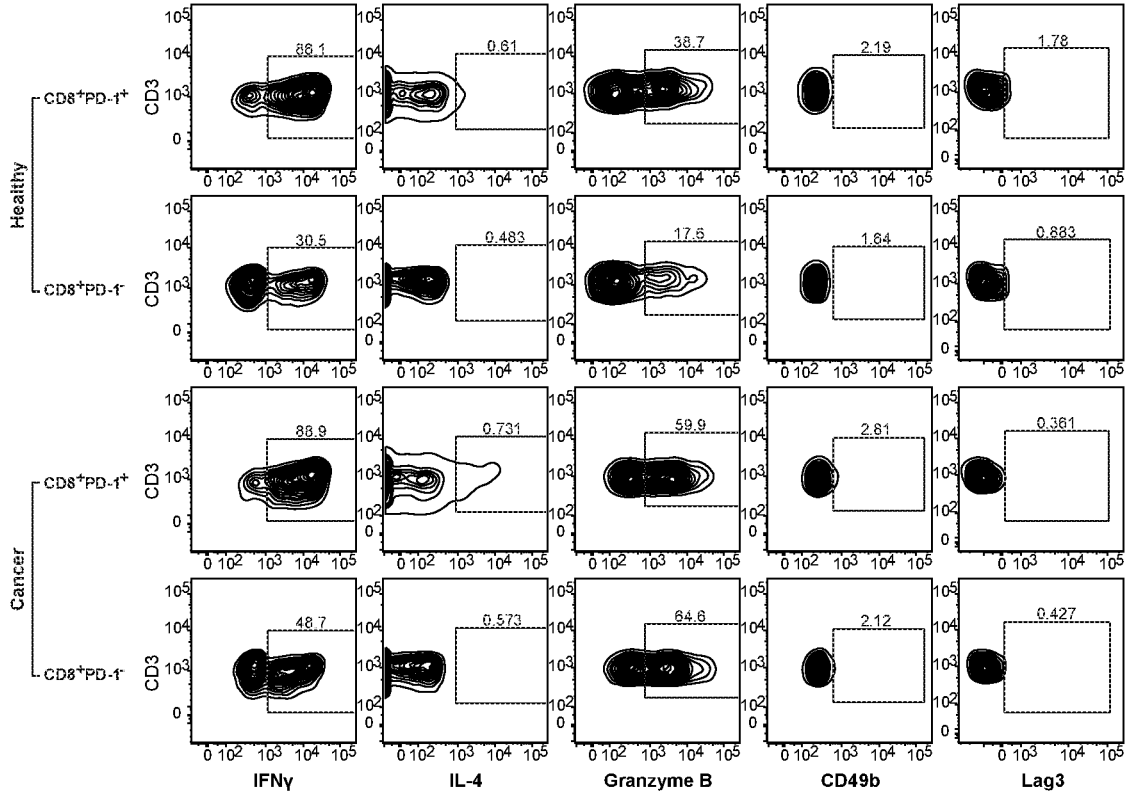

For mCRPC patients, age, baseline PSA levels, LDH levels, months on study, did not relate with OS (p-values=0.193, 0.311, 0.277, and 0.100 respectively). The number of patients with ECOG status of 0 or 1, Gleason scores grouped as 3 to 6, or 7 to 9, prior radical prostatectomy, and prior radiation, were not significantly different between the two groups (p-values=1.00, 0.90, 1.00, and 0.67 respectively). The number of patients with clinical responses as described above and the number of patients who went on to subsequent therapies also did not correlate with OS (p-values=0.16 and 0.38 respectively) (FIG. 11).

Figure 12:
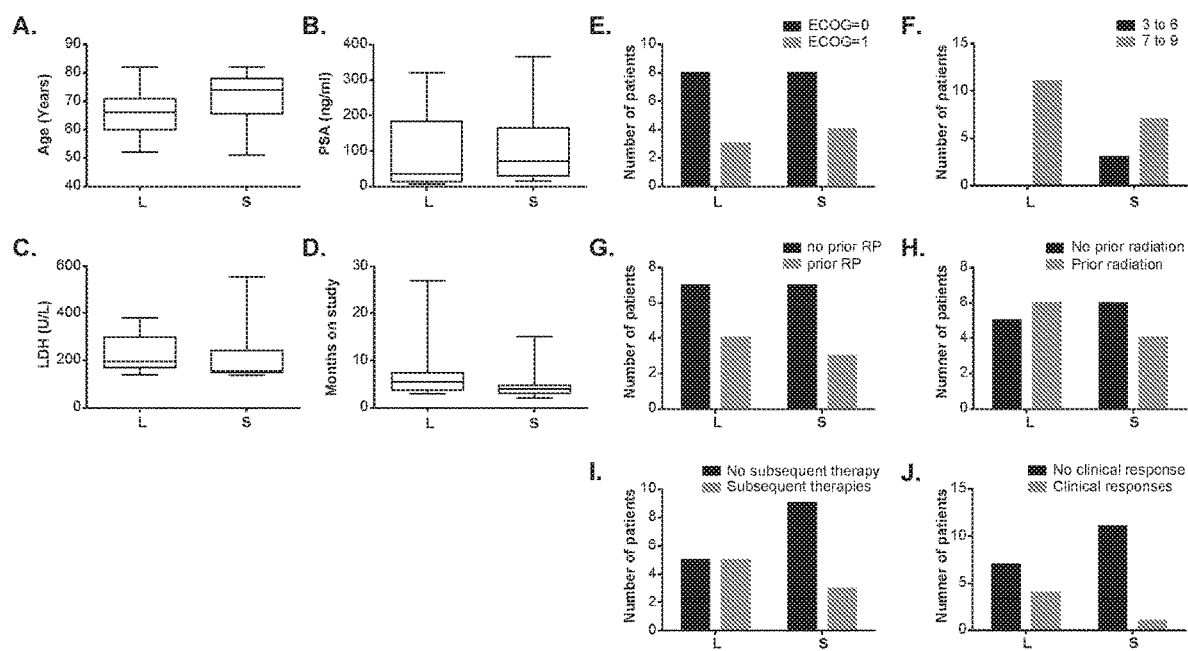
FIG. 12. Baseline characteristics for mCRPC patients. A, B, C, and D, Box plots of age, baseline PSA levels, LDH levels, and months on study respectively for long-term (L) and short-term (S) survivors. Whiskers show minimum and maximum levels. E, F, G, H, I, and J, Bar graphs showing the number of patients with the attributes designated in the legends for ECOG, Gleason score, prior RP, prior radiation, subsequent therapies, and clinical responses, respectively, for long-term (L) and short-term (S) survivors.
Figure 13:
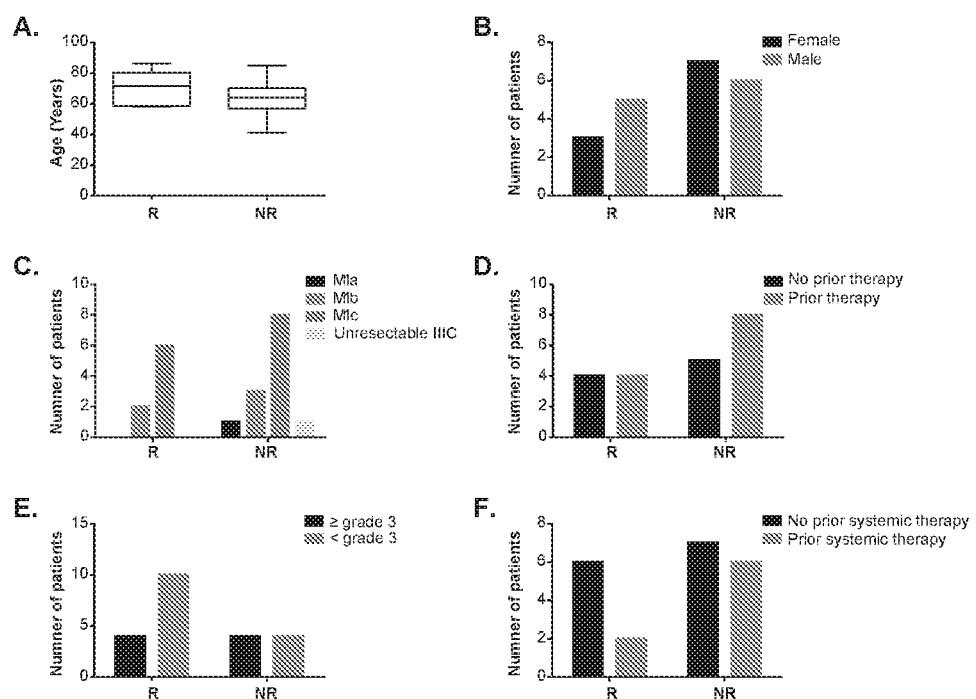
FIG. 13. Baseline characteristics for metastatic melanoma patients. A, Box plot of age for responders (R) and non-responders (NR). Whiskers show minimum and maximum levels. B, C, D, E, and F, Bar graphs showing the number of patients with the attributes designated in the legends for sex, tumor stage, prior therapy, immune adverse events, and prior systemic therapy respectively for responders (R) and non-responders (NR).

For metastatic melanoma, age, sex, tumor stage, prior therapy, immune adverse events, and prior systemic therapy did not relate significantly with either responders (R) or non-responders (NR) (p-values=0.23, 0.66, 0.71, 0.67, 0.39, and 0.40 respectively) (FIG. 12).

Example 6

Figure 7:
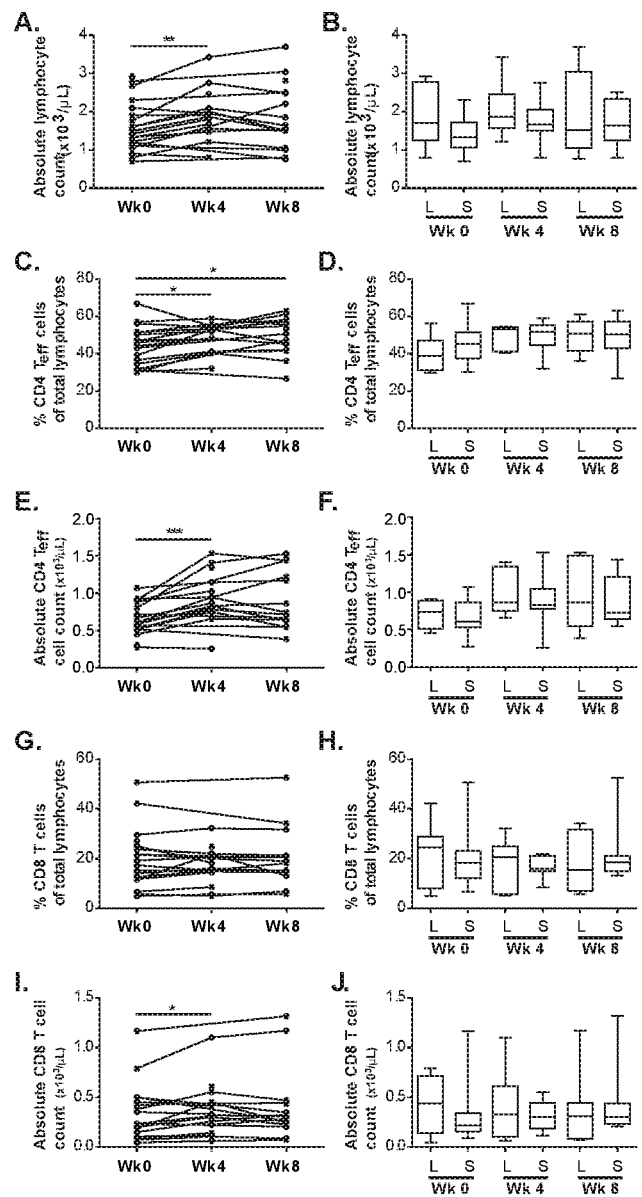
FIG. 7. Levels of circulating lymphocytes, CD4 $T_{eff}$ cells and CD8 T cells with treatment for mCRPC patients. A, Time course of absolute lymphocyte counts for assessed patients at week 0 (pre-treatment), week 4 (cycle 1), and week 8 (cycle 2) of treatment. Connected dots show time course of the same patient. B, Box plots of absolute lymphocyte counts for long-term (L) and short-term (S) survivors at each time point. C and G, Time course of percentage of CD4 $T_{eff}$ cells and CD8 T cells of total lymphocytes, respectively. Connected dots show time course of the same patient. E and I, Time course of absolute counts of CD4 $T_{eff}$ cells and CD8 T cells respectively. D and H, Box plots of percentage of CD4 $T_{eff}$ cells and CD8 T cells of total lymphocytes respectively for long-term (L) and short-term (S) survivors at each time point. F and J, Box plots of absolute counts of CD4 $T_{eff}$ cells and CD8 T cells respectively for long-term (L) and short-term (S) survivors at each time point. Whiskers show minimum and maximum levels. * p-value <0.05,  p-value <0.01, * p-value <0.001.

Absolute Lymphocyte Counts Did not Associate with Survival for mCRPC Patients or Clinical Responses for Metastatic Melanoma Patients For mCRPC patients, the absolute lymphocyte counts were significantly higher compared to pre-treatment levels after cycle 1 but not after cycle 2 of treatment (p-values=0.002 and 0.119 respectively) (FIG. 7A). The distribution of the absolute lymphocyte counts however did not differ between LTS and STS at pre-treatment (p-value=0.201), after cycle 1 (p-value=0.670), and after cycle 2 of treatment (p-value=0.779) (FIG. 7B).

Figure 8:
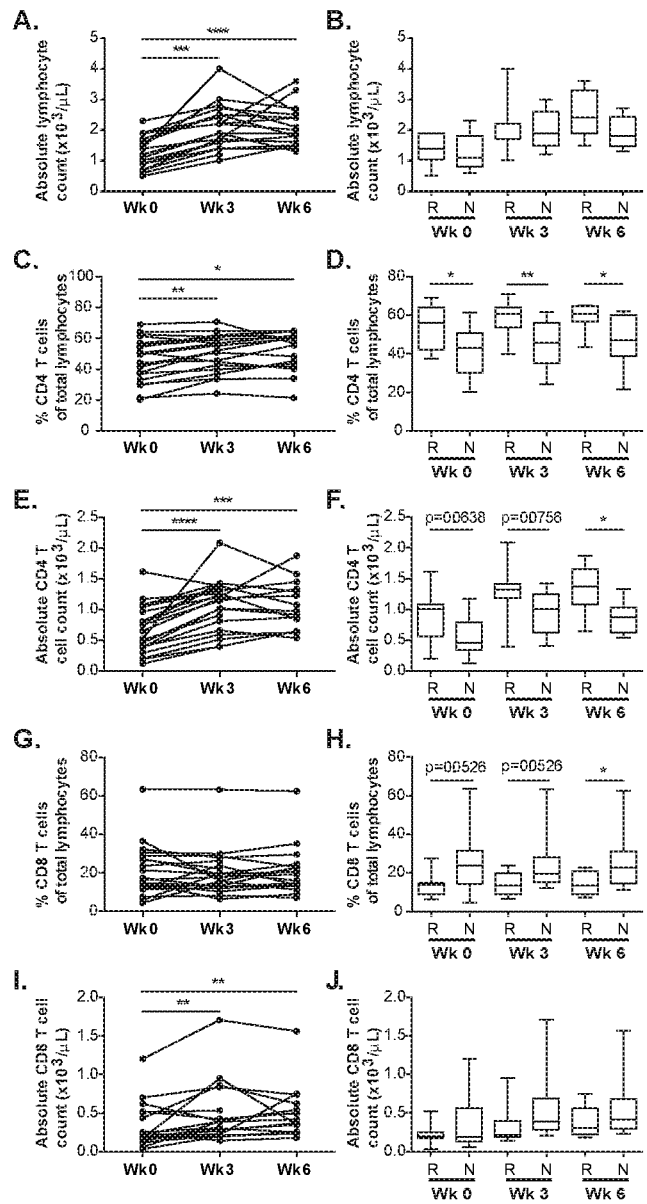
FIG. 8. Levels of circulating lymphocytes, CD4 T cells and CD8 T cells with treatment for metastatic melanoma patients. A, Time course of absolute lymphocyte counts for assessed patients at week 0 (pre-treatment), week 3 (cycle 1), and week 6 (cycle 2) of treatment. Connected dots show time course of the same patient. B, Box plots of absolute lymphocyte counts for responders plus SD (R) and non-responders (N) at each time point. C and G, Time course of percentage of CD4 T cells and CD8 T cells of total lymphocytes respectively. Connected dots show time course of the same patient. E and I, Time course of absolute counts of CD4 T cells and CD8 T cells respectively. D and H, Box plots of percentage of CD4 T cells and CD8 T cells of total lymphocytes respectively for responders plus SD (R) and non-responders (N) at each time point. F and J, Box plots of absolute counts of CD4 T cells and CD8 T cells respectively for responders plus SD (R) and non-responders (N) at each time point. Whiskers show minimum and maximum levels. * p-value <0.05,  p-value <0.01, * p-value <0.001.

For metastatic melanoma patients, the absolute lymphocyte counts were significantly higher compared to pre-treatment levels after cycle 1 and after cycle 2 of treatment (p-values=0.0002 and <0.0001 respectively) (FIG. 8A). The distribution of the absolute lymphocyte counts however did not differ between R and NR at pre-treatment (p-value=0.753), after cycle 1 (p-value=0.983), and after cycle 2 of treatment (p-value=0.126) (FIG. 8B).

Example 7

Relationship of CD4 $T_{eff}$ Cells, Total CD4 T Cells and CD8 T Cells with Survival or Clinical Responses.

For mCRPC, the percentages of total lymphocytes and absolute counts of CD4 $T_{eff}$ cells (CD4$^+$CD3$^+$ FoxP3$^-$) were significantly higher after one cycle of treatment (FIGS. 7C and E). However, for CD8 T cells, only the absolute counts and not the percentage of total lymphocytes, were significantly higher after one cycle of treatment (FIGS. 7G and I). This difference could be due to the higher levels of absolute lymphocyte counts after one cycle of treatment as described above.

For mCRPC patients, the distribution of the percentages of total lymphocytes and absolute counts of CD4 $T_{eff}$ cells did not differ between LTS and STS at pre-treatment (p-values=0.263 and 0.841 respectively), after cycle 1 (p-values=0.805 and 0.745 respectively), and after cycle 2 of treatment (p-values=0.920 and 0.845 respectively) (FIG. 7D, F). The percentages of total lymphocytes and absolute counts of CD8 T cells also did not relate with survival at pre-treatment (p-values=0.461 and 0.304 respectively), after cycle 1 (p-values=0.555 and 0.670 respectively), and after cycle 2 of treatment (p-values=0.671 and 0.835 respectively) (FIG. 7H, J).

For metastatic melanoma patients, the percentages of total lymphocytes and absolute counts of total CD4 T cells (CD8$^-$CD3$^+$) were significantly higher after 1 and 2 cycles of treatment (FIGS. 8C and E). The percentages of total lymphocytes and absolute counts of total CD8 T cells (CD8$^+$ CD3$^+$) were significantly higher after 1 and 2 cycles of treatment (FIGS. 8G and I).

The distribution of the percentages of total lymphocytes but not the absolute count of CD4 T cells did not differ between R and NR at pre-treatment (p-values=0.025 and 0.064 respectively), was significantly different for percentages but not absolute counts after cycle 1 (p-values=0.008 and 0.076 respectively), and was significantly different for both percentages and absolute counts after cycle 2 of treatment (p-values=0.033 and 0.026, respectively) (FIG. 8D, F). The percentages of total lymphocytes and absolute counts of CD8 T cells did not relate with clinical responses at pre-treatment (p-values=0.053 and 0.886). The percentages of total lymphocytes and absolute counts of CD8 T cells after cycle 1 did not correlate with clinical responses (p-values=0.053 and 0.074, respectively). The percentages of total lymphocyte but not the absolute counts of CD8 T cells related significantly with clinical responses after cycle 2 of treatment (p-values=0.035 and 0.372, respectively) (FIG. 8H, J).

Example 8

Figure 4:
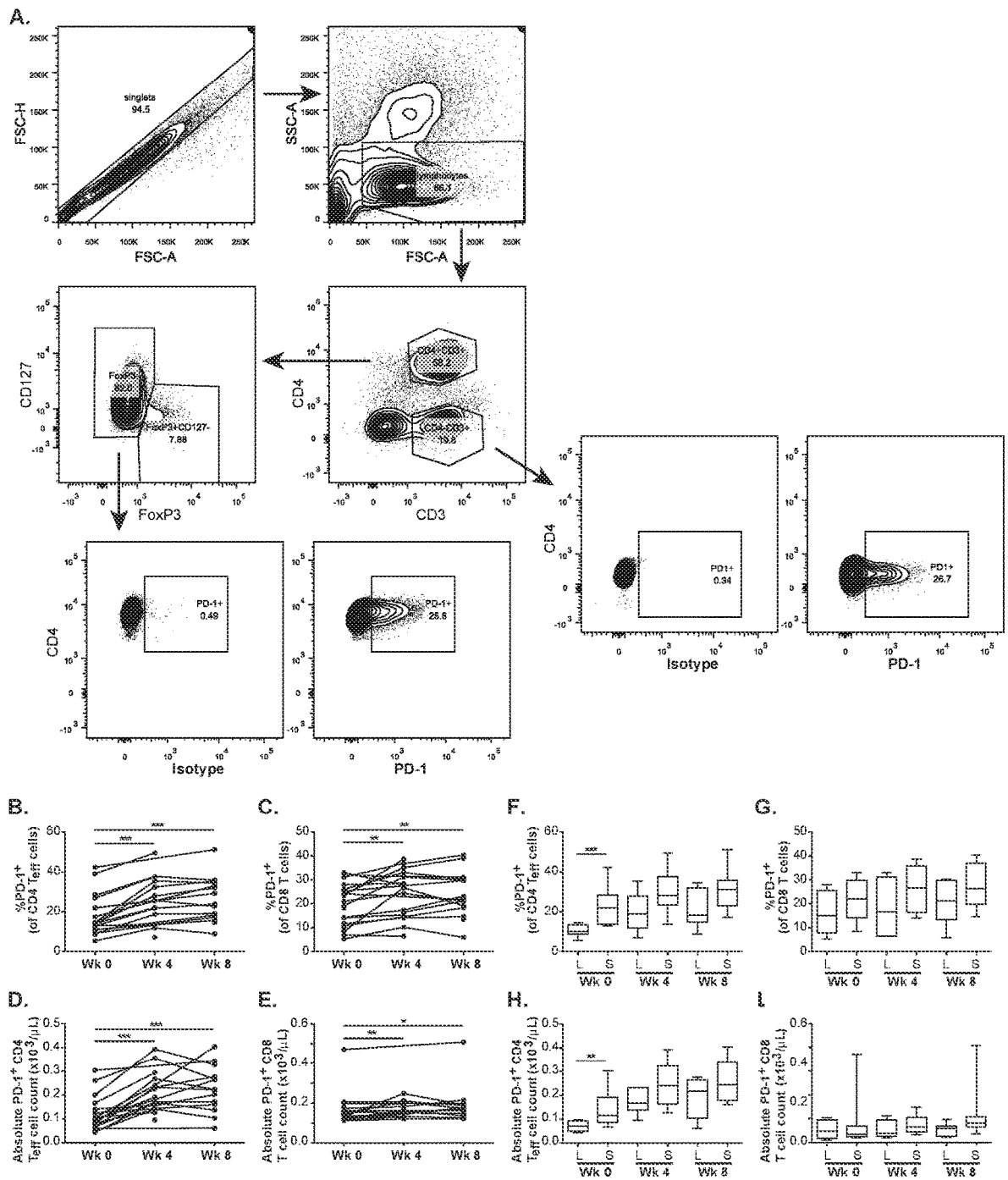
FIG. 4. Surface PD-1 expression of CD4 $T_{eff}$ cells and CD8 T cells for mCRPC patients. A, Flow cytometry was used to assess PD-1 expression by CD4 $T_{eff}$ cells and CD8 T cells. Percentage of PD-1 positive cells in antibody-stained sample was gated based on isotype-containing controls. Shaded histograms denote isotype controls; open histograms denote stained samples. B and C, Time course of percentage of CD4 $T_{eff}$ and CD8 T cells that express PD-1 respectively. Connected dots show time course of the same patient. D and E, Time course of absolute counts of CD4 $T_{eff}$ and CD8 T cells that express PD-1 respectively. F and G, Box plots of percentage of CD4 $T_{eff}$ and CD8 T cells that express PD-1 respectively for long-term (L) and short-term (S) survivors at each time point. H and I, Box plots of absolute counts of CD4 $T_{eff}$ and CD8 T cells that express PD-1 respectively for long-term (L) and short-term (S) survivors at each time point. Whiskers show minimum and maximum levels. * p-value <0.05,  p-value <0.01, * p-value <0.001.

Lower Pre-Treatment Levels of PD-1$^+$ CD4 Effector T Cells Associate with Longer Survival for mCRPC Patients and with Clinical Responses for Metastatic Melanoma Patients For mCRPC patients, the percentages of CD4 $T_{eff}$ cells that express surface PD-1 were significantly higher after cycle 1 (p-value=0.0001) and continued to be significantly higher after cycle 2 compared to pre-treatment levels (p-value=0.0002) (FIG. 4A, B, D). The absolute counts of PD-1+CD4 $T_{eff}$ cells were also significantly higher after both cycles (p-values=0.0001 and 0.0002 respectively). The percentages of CD8 T cells that express PD-1 were also significantly higher from pre-treatment levels after cycle 1 (p-value=0.004) and after cycle 2 of treatment (p-value=0.005) (FIG. 4A, C, E). The absolute counts of PD-1$^+$ CD8 T cells were also significantly higher after both cycles (p-values=0.005 and 0.022 respectively).

For mCRPC patients, the distribution of the percentages of surface PD-1+ on CD4 $T_{eff}$ cells and absolute counts of PD-1$^+$ CD4 $T_{eff}$ at pre-treatment was significantly lower in LTS compared to STS (p-values=0.0007 and 0.003 respectively) (FIG. 4F, H). After treatment, the distribution of the percentages of surface PD-1$^+$ on CD4 $T_{eff}$ cells and absolute counts of PD-1$^+$ CD4 $T_{eff}$ were not significantly different between STS or LTS after cycle 1 (p-values=0.055 and 0.090 respectively) and after cycle 2 (p-values=0.054 and 0.150 respectively) (FIG. 4F, H). The distributions of the percentages and absolute counts of surface PD-1$^+$ CD8 T cells between STS and LTS did not differ at pre-treatment (p-value=0.246 and >0.999 respectively) or at any time point after treatment (FIG. 4A, G, I).

Figure 14:
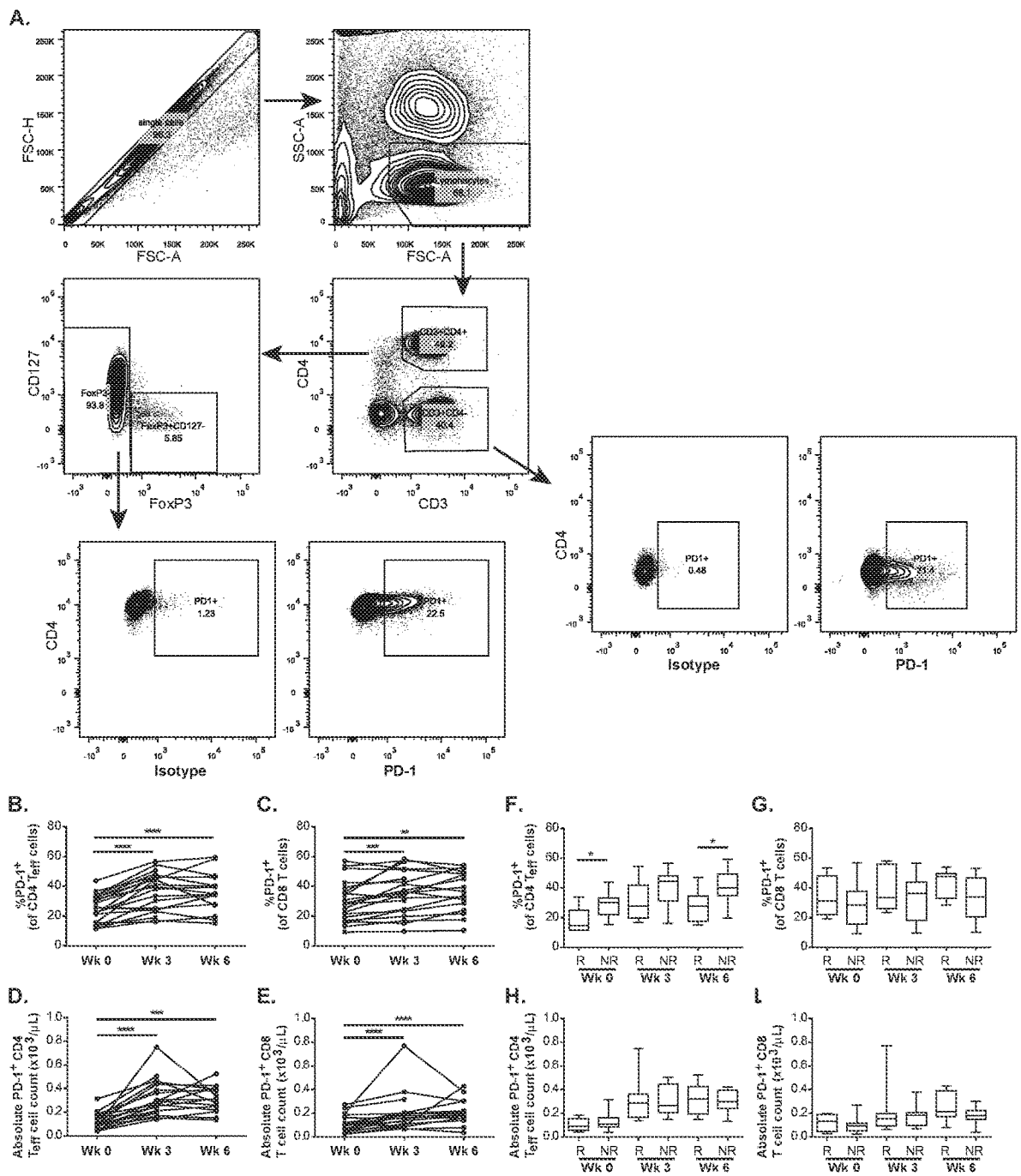
FIG. 14. Surface PD-1 expression of CD4 $T_{eff}$ cells and CD8 T cells for metastatic melanoma patients. A, Flow cytometry was used to assess PD-1 expression by CD4 $T_{eff}$ cells and CD8 T cells. Percentage of PD-1-positive cells in antibody-stained sample was gated based on isotype-containing controls. Shaded histograms denote isotype controls; open histograms denote stained samples. B and C, Time course of percentage of CD4 $T_{eff}$ and CD8 T cells that express PD-1, respectively. Connected dots show time course of the same patient. D and E, Time course of absolute counts of CD4 $T_{eff}$ and CD8 T cells that express PD-1, respectively. F and G, Box plots of percentage of CD4 $T_{eff}$ and CD8 T cells that express PD-1, respectively, for responders (R) and non-responders (NR) at each time point. H and I, Box plots of absolute counts of CD4 $T_{eff}$ and CD8 T cells that express PD-1, respectively, for responders (R) and non-responders (NR) at each time point. Whiskers show minimum and maximum levels. * p-value <0.05,  p-value <0.01, * p-value <0.001.

For metastatic melanoma patients, the percentages of CD4 $T_{eff}$ cells that express surface PD-1 similarly increased after cycle 1 and cycle 2 (p-values=<0.0001 for both). The absolute counts of PD-1$^+$ CD4 $T_{eff}$ cells were similarly higher after both cycles (p-values=<0.0001 and 0.0001 respectively). The percentages of CD8 T cells that express PD-1 were also significantly higher from pre-treatment levels after cycle 1 (p-value=0.001) and after cycle 2 of treatment (p-value=0.003). The absolute counts of PD-1$^+$ CD8 T cells were also significantly higher after both cycles (p-values=<0.0001 for both) (FIG. 14).

For metastatic melanoma patients, the distribution of the percentages of surface PD-1+ on CD4 $T_{eff}$ cells but not the absolute counts of PD-1$^+$ CD4 $T_{eff}$ at pre-treatment was significantly lower in R compared to NR (p-values=0.017 and 0.887, respectively). The distribution of the percentages of surface PD-1+ on CD4 $T_{eff}$ cells but not the absolute counts of PD-1$^+$ CD4 $T_{eff}$ after cycle 2 was significantly lower in R compared to NR (p-values=0.040 and 0.946 respectively). The distributions of the percentages and absolute counts of surface PD-1$^+$ CD8 T cells between R and NR did not differ at pre-treatment (p-values=0.453 and 0.744 respectively) or at any time point after treatment (cycle 1 percentage and absolute count p-values=0.543 and 0.441; cycle 2 percentage and absolute count p-values=0.229 and 0.118).

Example 9

Figure 5:
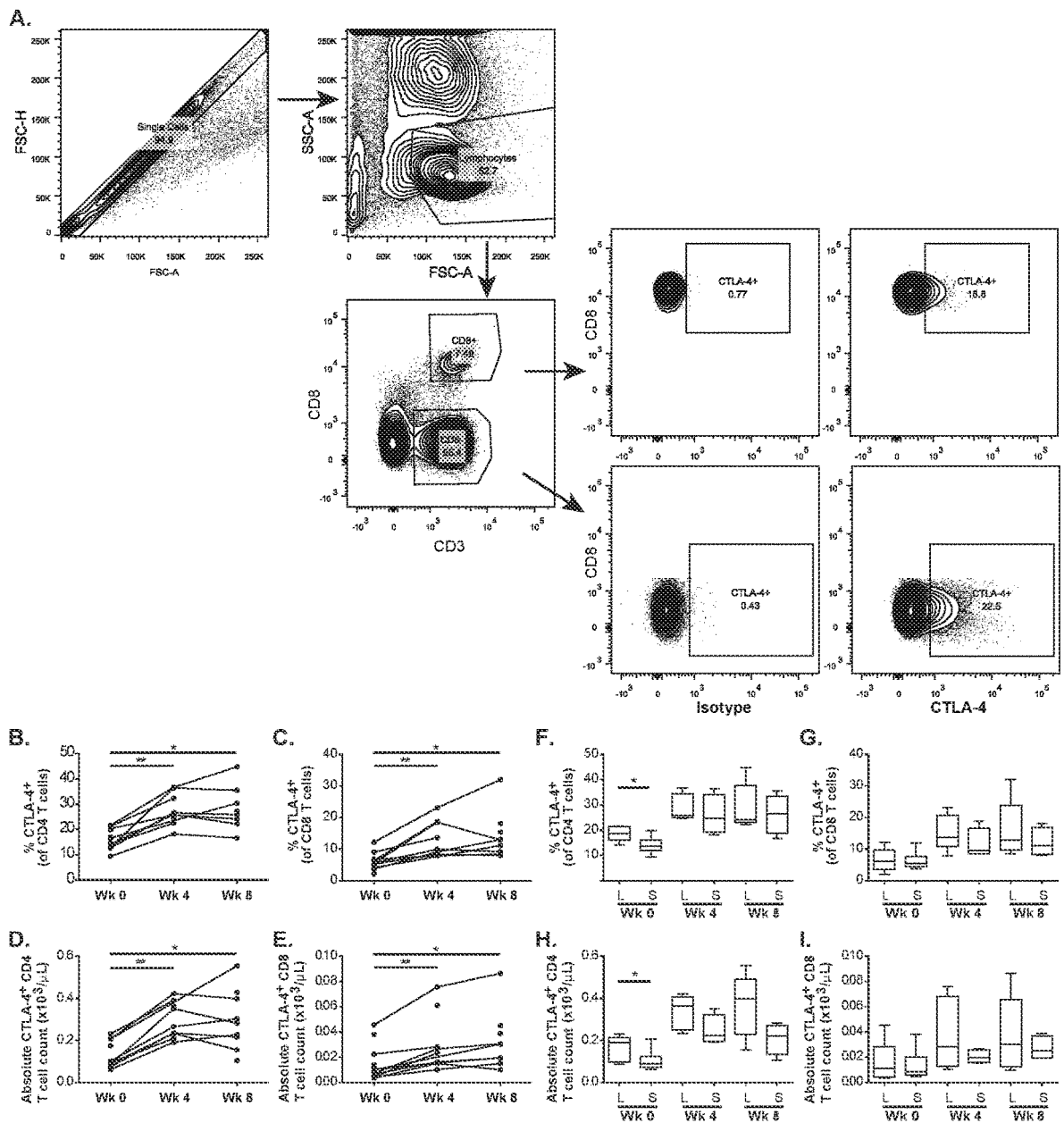
FIG. 5. Total CTLA-4$^+$ expression in total CD4 and CD8 T cells for mCRPC patients. A, Flow cytometry was used to assess CTLA-4 expression by CD4 T cells and CD8 T cells. Percentage of CTLA-4 positive cells in antibody-stained sample was gated based on isotype-containing controls. Shaded histograms denote isotype controls; open histograms denote stained samples. B and C, Time course of percentage of CD4 T and CD8 T cells that express CTLA-4 respectively. Connected dots show time course of the same patient. D and E, Time course of absolute counts of CD4 T and CD8 T cells that express CTLA-4 respectively. F and G, Box plots of percentage of CD4 T and CD8 T cells that express CTLA-4 respectively for long-term (L) and short-term (S) survivors at each time point. H and I, Box plots of absolute counts of CD4 T and CD8 T cells that express CTLA-4 respectively for long-term (L) and short-term (S) survivors at each time point. Whiskers show minimum and maximum levels. * p-value <0.05,  p-value <0.01, * p-value <0.001.

High Pre-Treatment Levels of CLTA-4$^+$ CD4 T Cells Associate with Improved Survival For mCRPC patients, the percentages of CTLA-4$^+$ of CD4 T cells increased significantly after cycle 1 (p-value=0.0078) and after cycle 2 (p-value=0.016) of treatment (FIGS. 5A, and B). The absolute counts of CTLA-4$^+$ CD4 T cells also increased significantly after cycle 1 (p-value=0.0078) and after cycle 2 (p-value=0.016) of treatment (FIG. 5D). The percentages of CTLA-4$^+$ of CD8 T cells increased significantly after cycle 1 (p-value=0.0078) and after cycle 2 (p-value=0.016) of treatment (FIGS. 5A, and C). The absolute counts of CTLA-4$^+$ CD8 T cells also increased significantly after cycle 1 (p-value=0.0078) and after cycle 2 (p-value=0.016) of treatment (FIG. 5E).

For mCRPC patients, higher pre-treatment percentages of CTLA-4$^+$ of CD4 T cells at pre-treatment related with long-term survivors (p-value=0.030) but not after cycle 1 or cycle 2 of treatment (p-values=0.524 and >0.999 respectively) (FIG. 5F). The pre-treatment absolute CTLA-4$^+$ CD4 T cell count was also significantly different between LTS and STS at pre-treatment (p-value=0.0411) (FIG. 5H) but not after cycle 1 or cycle 2 of treatment (p-values=0.111 for both). The distribution of the percentages of CTLA-4$^+$ of CD8 T cells at pre-treatment or after cycles 1 or 2 did not relate with long-term survivors (p-values=0.788, 0.508, and 0.683 respectively) (FIG. 5G). The pre-treatment absolute CTLA-4$^+$ CD8 T cell count was also not significantly different between LTS and STS at pre-treatment or after cycles 1 or 2 (p-values=>0.999, 0.83, and >0.999 respectively) (FIG. 5I).

Example 10

Figure 6:
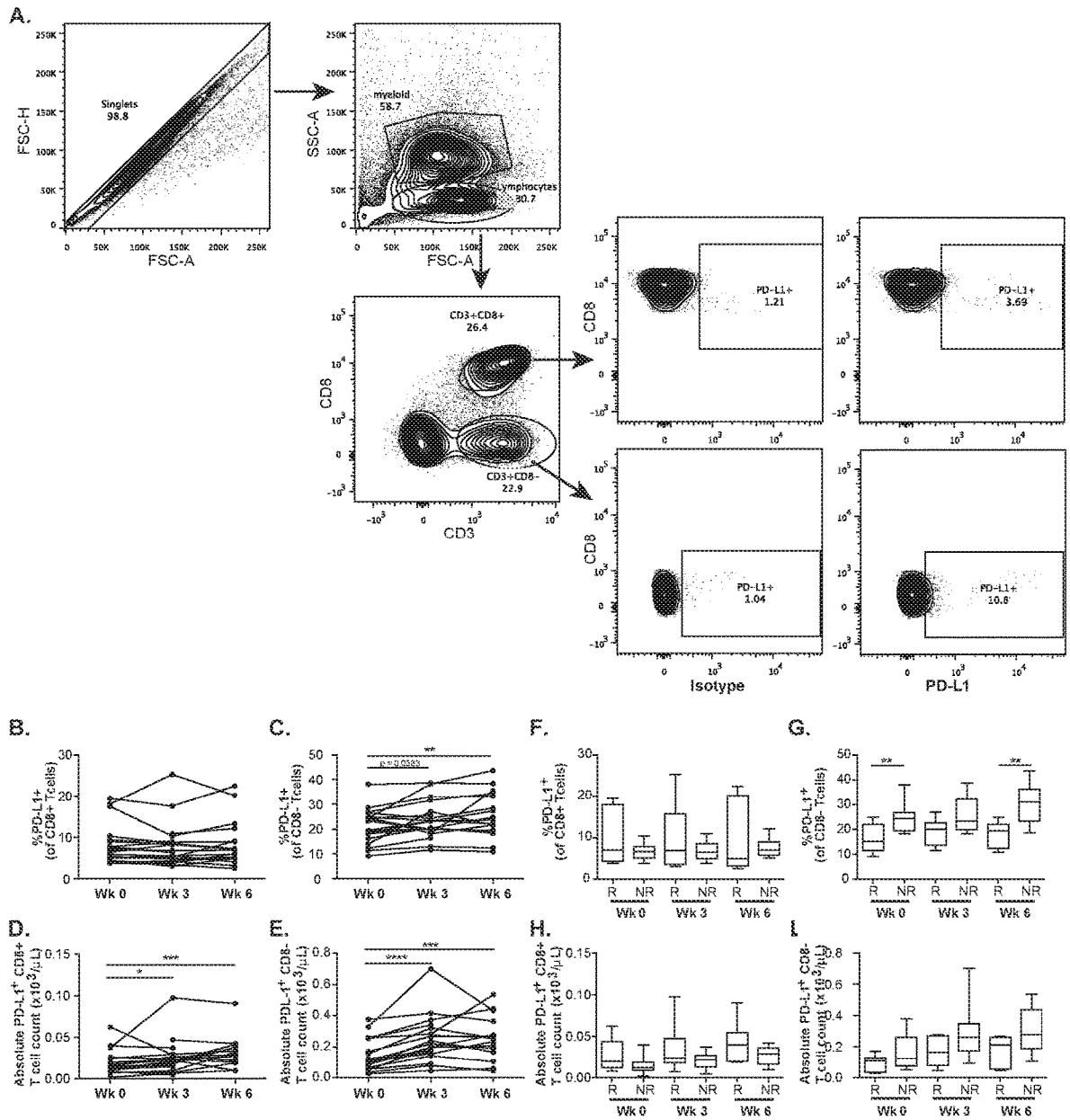
FIG. 6. Surface PD-L1 expression of CD4 cells and CD8 T cells for metastatic melanoma patients. A, Flow cytometry was used to assess PD-L1 expression by CD4 T cells and CD8 T cells. Percentage of PD-L1 positive cells in antibody-stained sample was gated based on isotype-containing controls. Shaded histograms denote isotype controls; open histograms denote stained samples. B and C, Time course of percentage of CD8 T and CD4 T cells that express PD-L1 respectively. Connected dots show time course of the same patient. D and E, Time course of absolute counts of CD8 T and CD4 T cells that express PD-L1 respectively. F and G, Box plots of percentage of CD4 T and CD8 T cells that express PD-L1 respectively for responders (R) and non-responders (NR) at each time point. H and I, Box plots of absolute counts of CD8 T and CD4 T cells that express PD-L1 respectively for responders (R) and non-responders (NR) at each time point. Whiskers show minimum and maximum levels. * p-value <0.05,  p-value <0.01, * p-value <0.001, **** p-value <0.0001.

Lower Pre-Treatment Levels of PD-L1$^+$ CD4 Effector T Cells Associate with Clinical Responses for Metastatic Melanoma Patients For metastatic melanoma patients, the percentages of PD-L1$^+$ of CD4 T cells did not increased significantly after cycle 1 (p-value=0.058) but increased significantly after cycle 2 (p-value=0.004) of treatment (FIGS. 6A, and B). The absolute counts of PD-L1$^+$ CD4 T cells increased significantly after cycle 1 (p-value=<0.0001) and after cycle 2 (p-value=0.0004) of treatment (FIG. 6D). The percentages of PD-L1$^+$ of CD8 T cells did not increased significantly after cycle 1 (p-value=0.202) and after cycle 2 (p-value=0.562) of treatment (FIGS. 6A, and C). The absolute counts of PD-L1$^+$ CD8 T cells increased significantly after cycle 1 (p-value=0.012) and after cycle 2 (p-value=0.001) of treatment (FIG. 6E).

For metastatic melanoma patients, lower pre-treatment percentages of PD-L1$^+$ of CD4 T cells at pre-treatment and after cycle 2 related with clinical responses (p-values=0.006 and 0.007 respectively) but not after cycle 1 of treatment (p-value=0.087) (FIG. 6F). The pre-treatment absolute PD-L1$^+$ CD4 T cell count was not significantly different between R and NR at pre-treatment (p-value=0.268) (FIG. 6H) or after cycle 1 or cycle 2 of treatment (p-values=0.065 and 0.111 respectively). The distribution of the percentages of PD-L1$^+$ of CD8 T cells at pre-treatment or after cycles 1 or 2 did not relate with clinical responses (p-values=0.727, 0.962, and 0.643 respectively) (FIG. 6G). The pre-treatment absolute PD-L1$^+$ CD8 T cell count was also not significantly different between R and NR at pre-treatment or after cycles 1 or 2 (p-values=0.244, 0.399, and 0.181 respectively) (FIG. 6I).

Example 11

Figure 9:
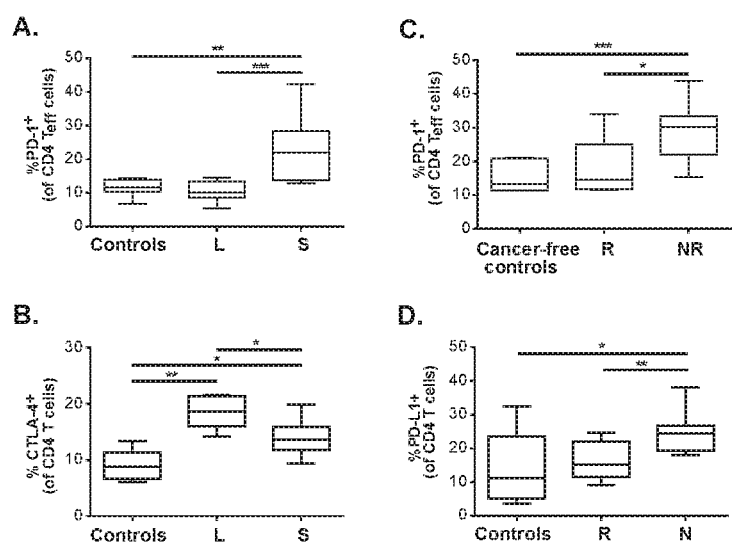
FIG. 9. Comparison of PD-1, CTLA-4 and PD-L1 expression levels between cancer-free controls and cancer patients at baseline. A, Box plots of percentage of CD4 $T_{eff}$ cells that express PD-1 for cancer-free controls (Controls), long-term (L) and short-term (S) survivors for mCRPC. B, Box plots of percentage of total CD4 T cells that express CTLA-4 for cancer-free controls (Controls), long-term (L) and short-term (S) survivors for mCRPC. C, Box plots of percentage of CD4 $T_{eff}$ cells that express PD-1 for cancer-free controls (Controls), responders (R) and non-responders (N) for metastatic melanoma. D, Box plots of percentage of total CD4 T cells that express PD-L1 for cancer-free controls (Controls), responders (R) and non-responders (N) for metastatic melanoma. Whiskers show minimum and maximum levels. * p-value <0.05,  p-value <0.01, * p-value <0.001.

Comparison with Cancer-Free Controls mCRPC patients with poorer survival have significantly higher pre-treatment levels of PD-1$^+$ CD4 T$_{eff}$ cells compared to cancer-free controls (p-value=0.001), whereas patients with better survival have similar pre-treatment levels of PD-1$^+$ CD4 T$_{eff}$ cells compared to cancer-free controls (FIG. 9A).

mCRPC patients with poorer survival have similar or slightly higher pre-treatment levels of CTLA-4$^+$ CD4 T cells compared to cancer-free controls, whereas patients with better survival have significantly higher pre-treatment levels of CTLA-4$^+$ CD4 T cells compared to cancer-free controls (p-value=0.001) (FIG. 9B).

Metastatic melanoma patients with progressive disease have significantly higher pre-treatment levels of PD-1$^+$ CD4 T$_{eff}$ cells compared to cancer-free controls (p-value=0.0002), whereas patients with clinical responses or stable disease have similar pre-treatment levels of PD-L1$^+$ CD4 T cells compared to cancer-free controls (FIG. 9C).

Metastatic melanoma patients with progressive disease have significantly higher pre-treatment levels of PD-L1$^+$ CD4 T cells compared to cancer-free controls (p-value=0.047), whereas patients with clinical responses or stable disease have similar pre-treatment levels of PD-L1$^+$ CD4 T cells compared to cancer-free controls (FIG. 9D).

Example 12

Summary of Significance Values

Percentages of Immune Subsets

TABLE 6

Comparison of pre-treatment T cell subsets

| mCRPC patients | LTS (n = 8) Median$^a$ (Range$^b$) | STS (n = 12) Median$^a$ (Range$^b$) | p-value$^c$ |
|---|---|---|---|
| Total CD4 T cells (CD4$^+$CD3$^+$) | 41.0 (32.8-59.6) | 48.3 (33.6-71.8) | 0.203 |
| CD4 T$_{eff}$ cells (CD4$^+$CD3$^+$FoxP3$^-$) | 38.9 (30.1-56.2) | 45.2 (30.4-66.8) | 0.263 |
| PD-1$^+$CD4$^+$CD3$^+$FoxP3$^-$ | 10.1 (5.4-14.5) | 22.0 (12.8-42.3) | 0.0007 |
| Total CD8 T cells (CD4$^-$CD3$^+$) | 24.5 (5.0-42.2) | 18.3 (6.7-50.7) | 0.461 |
| PD-1$^+$CD4$^-$CD3$^+$ | 15.0 (5.3-28.0) | 22.2 (8.4-33.0) | 0.246 |

| mCRPC patients | LTS (n = 6) Median$^a$ (Range$^b$) | STS (n = 6) Median$^a$ (Range$^b$) | p-value$^c$ |
|---|---|---|---|
| Total CD4 T cells (CD8$^-$CD3$^+$) | 43.0 (35.2-58.9) | 51.7 (40.6-61.9) | 0.305 |
| CTLA-4$^+$CD8$^-$CD3$^+$ | 18.7 (14.2-21.6) | 13.7 (9.4-19.9) | 0.030 |
| Total CD8 T cells (CD8$^+$CD3$^+$) | 10.8 (4.2-25.0) | 12.9 (5.4-24.5) | 0.675 |
| CTLA-4$^+$CD8$^+$CD3$^+$ | 6.2 (2.1-12.2) | 5.5 (3.7-12.0) | 0.788 |

| Metastatic melanoma patients | R (n = 8) Median$^a$ (Range$^b$) | NR (n = 13) Median$^a$ (Range$^b$) | p-value$^c$ |
|---|---|---|---|
| CD4 T$_{eff}$ cells (CD4$^+$CD3$^+$FoxP3$^-$) | 46.9 (24.3-58.9) | 38.2 (19.1-53.6) | 0.104 |
| PD-1$^+$CD4$^+$CD3$^+$FoxP3$^-$ | 14.6 (11.5-33.9) | 30.2 (15.4-43.8) | 0.017 |
| Total CD8 T cells (CD4$^-$CD3$^+$) | 18.9 (13.3-39.6) | 29.8 (16.4-64.4) | 0.157 |
| PD-1$^+$CD4$^-$CD3$^+$ | 31.2 (19.2-53.4) | 28.5 (9.3-56.9) | 0.453 |
| Total CD4 T cells (CD8$^-$CD3$^+$) | 56.1 (37.4-69.1) | 43.0 (20.4-61.6) | 0.025 |
| PD-L1$^+$CD8$^-$CD3$^+$ | 15.1 (9.2-24.7) | 24.4 (18.1-38.1) | 0.006 |
| Total CD8 T cells (CD8$^+$CD3$^+$) | 13.7 (6.1-27.3) | 23.7 (4.5-63.4) | 0.053 |
| PD-L1$^+$CD8$^+$CD3$^+$ | 7.0 (3.9-19.4) | 6.7 (3.8-10.3) | 0.727 |

$^a$Median values of parent gates are % of total lymphocytes and median values of immune checkpoint markers are % of the respective parent gate;
$^b$Values in brackets ( ) are range of each data set;
$^c$Mann-Whitney test;
Bold-faced characters highlight p-value ≤ 0.05;
LTS, long-term survivors; STS, short-term survivors; R, clinical responders; NR, non-responders.

Absolute Counts of Immune Subsets

TABLE 7

Comparison of pre-treatment absolute counts of T cell subsets

| mCRPC patients | LTS (n = 8) Median$^a$ (Range$^b$) | STS (n = 12) Median$^a$ (Range$^b$) | p-value$^c$ |
|---|---|---|---|
| Total CD4 T cells (CD4$^+$CD3$^+$) | 0.80 (0.48-0.99) | 0.64 (0.33-1.15) | 0.841 |
| CD4 T$_{eff}$ cells (CD4$^+$CD3$^+$FoxP3$^-$) | 0.74 (0.45-0.91) | 0.61 (0.27-1.07) | 0.841 |
| PD-1$^+$CD4$^+$CD3$^+$FoxP3$^-$ | 0.07 (0.04-0.10) | 0.12 (0.07-0.30) | 0.003 |
| Total CD8 T cells (CD4$^-$CD3$^+$) | 0.44 (0.05-0.79) | 0.22 (0.09-1.17) | 0.304 |
| PD-1$^+$CD4$^-$CD3$^+$ | 0.05 (0.01-0.10) | 0.03 (0.02-0.37) | >0.999 |

TABLE 7-continued

Comparison of pre-treatment absolute counts of T cell subsets

| mCRPC patients | LTS (n = 6)<br>Median[a] (Range[b]) | STS (n = 6)<br>Median[a] (Range[b]) | p-value[c] |
|---|---|---|---|
| Total CD4 T cells (CD8⁻CD3⁺) | 1.02 (0.62-1.25) | 0.65 (0.60-1.03) | 0.387 |
| CTLA-4⁺CD8⁻CD3⁺ | 0.19 (0.09-0.23) | 0.09 (0.06-0.20) | 0.041 |
| Total CD8 T cells (CD8⁺CD3⁺) | 0.24 (0.03-0.67) | 0.19 (0.07-0.32) | 0.788 |
| CTLA-4⁺CD8⁺CD3⁺ | 0.01 (0.003-0.05) | 0.009 (0.005-0.04) | >0.999 |

| Metastatic melanoma patients | R (n = 8)<br>Median[a] (Range[b]) | NR (n = 13)<br>Median[a] (Range[b]) | p-value[c] |
|---|---|---|---|
| CD4 $T_{eff}$ cells (CD4⁺CD3⁺FoxP3⁻) | 0.80 (0.13-1.31) | 0.40 (0.12-1.08) | 0.064 |
| PD-1⁺CD4⁺CD3⁺FoxP3⁻ | 0.12 (0.06-0.25) | 0.11 (0.04-0.31) | 0.886 |
| Total CD8 T cells (CD4⁻CD3⁺) | 0.35 (0.10-0.75) | 0.26 (0.15-1.22) | 0.744 |
| PD-1⁺CD4⁻CD3⁺ | 0.10 (0.03-0.20) | 0.09 (0.03-27) | 0.744 |
| Total CD4 T cells (CD8⁻CD3⁺) | 1.01 (0.20-1.61) | 0.46 (0.12-1.17) | 0.064 |
| PD-L1⁺CD8⁻CD3⁺ | 0.11 (0.03-0.17) | 0.12 (0.05-0.38) | 0.268 |
| Total CD8 T cells (CD8⁺CD3⁺) | 0.20 (0.03-0.52) | 0.19 (0.06-1.21) | 0.886 |
| PD-L1⁺CD8⁺CD3⁺ | 0.02 (0.008-0.06) | 0.01 (0.002-0.04) | 0.244 |

[a]Median absolute counts of T cell subsets;
[b]Values in brackets ( ) are range of each data set;
[c]Mann-Whitney test;
Bold-faced characters highlight p-value ≤ 0.05;
LTS, long-term survivors; STS, short-term survivors; R, clinical responders; NR, non-responders.

Comparison with Cancer-Free Controls

TABLE 8

Comparison of pre-treatment T cell subsets between cancer-free controls and cancer patients

| | Groups | Median[d] (Range[e]) | p-value[f] | |
|---|---|---|---|---|
| mCRPC patients[a] | | | | |
| PD-1⁺ CD4 $T_{eff}$ cells | Cancer-free controls | 11.7 (6.7-14.3) | 0.456 | 0.002 |
| | LTS week 0 | 10.1 (5.4-14.5) | | |
| | STS week 0 | 22.2 (8.4-33.0) | 0.0007 | |
| PD-1⁺ CD8 T cells | Cancer-free controls | 13.7 (8.7-27.5) | 0.931 | 0.117 |
| | LTS week 0 | 15.0 (5.3-28.0) | | |
| | STS week 0 | 22.2 (8.4-33.0) | 0.246 | |
| mCRPC patients[b] | | | | |
| CTLA-4⁺ CD4 T cells | Cancer-free controls | 8.8 (6.1-13.4) | 0.001 | 0.022 |
| | LTS week 0 | 18.7 (14.2-21.6) | | |
| | STS week 0 | 13.7 (9.4-19.9) | 0.030 | |
| CTLA-4⁺ CD8 T cells | Cancer-free controls | 3.1 (3.0-10.6) | 0.363 | 0.138 |
| | LTS week 0 | 6.2 (2.1-12.2) | | |
| | STS week 0 | 5.5 (3.7-12.0) | 0.788 | |
| Metastatic melanoma patients[c] | | | | |
| PD-1⁺ CD4 $T_{eff}$ cells | Cancer-free controls | 13.3 (11.3-21.1) | 0.379 | 0.0002 |
| | R week 0 | 14.6 (11.5-33.9) | | |
| | NR week 0 | 30.2 (15.4-43.8) | 0.017 | |
| PD-1⁺ CD8 T cells | Cancer-free controls | 15.6 (9.2-26.8) | 0.009 | 0.058 |
| | R week 0 | 31.2 (19.2-53.4) | | |
| | NR week 0 | 28.5 (9.3-56.9) | 0.246 | |
| PD-L1⁺ CD4 T cells | Cancer-free controls | 11.1 (3.6-32.5) | 0.495 | 0.047 |
| | R week 0 | 15.1 (9.2-24.7) | | |
| | NR week 0 | 24.4 (18.1-38.1) | 0.006 | |

TABLE 8-continued

Comparison of pre-treatment T cell subsets between cancer-free controls and cancer patients

| | Groups | Median[d] (Range[e]) | p-value[f] | |
|---|---|---|---|---|
| PD-L1[+] CD8 T cells | Cancer-free controls | 2.9 (1.9-4.6) | 0.010 | 0.002 |
| | R week 0 | 5.0 (2.8-14.6) | | |
| | NR week 0 | 4.6 (2.7-6.0) | 0.341 | |

[a]cancer-free controls, n = 7, LTS, n = 8; STS, n = 12;
[b]cancer-free controls, n = 7, LTS, n = 6, STS, n—6;
[c]cancer-free controls, n = 8, R, n = 8, NR, n = 13;
[d]Median values of immune checkpoint markers are % of the respective parent gate;
[e]Values in brackets ( ) are range of each data set;
[f]Mann-Whitney test;
Bold-faced characters highlight p-value ≤ 0.05;
LTS, long-term survivors; STS, short-term survivors; R, clinical responders; NR, non-responders.

Example 13

Figure 10:
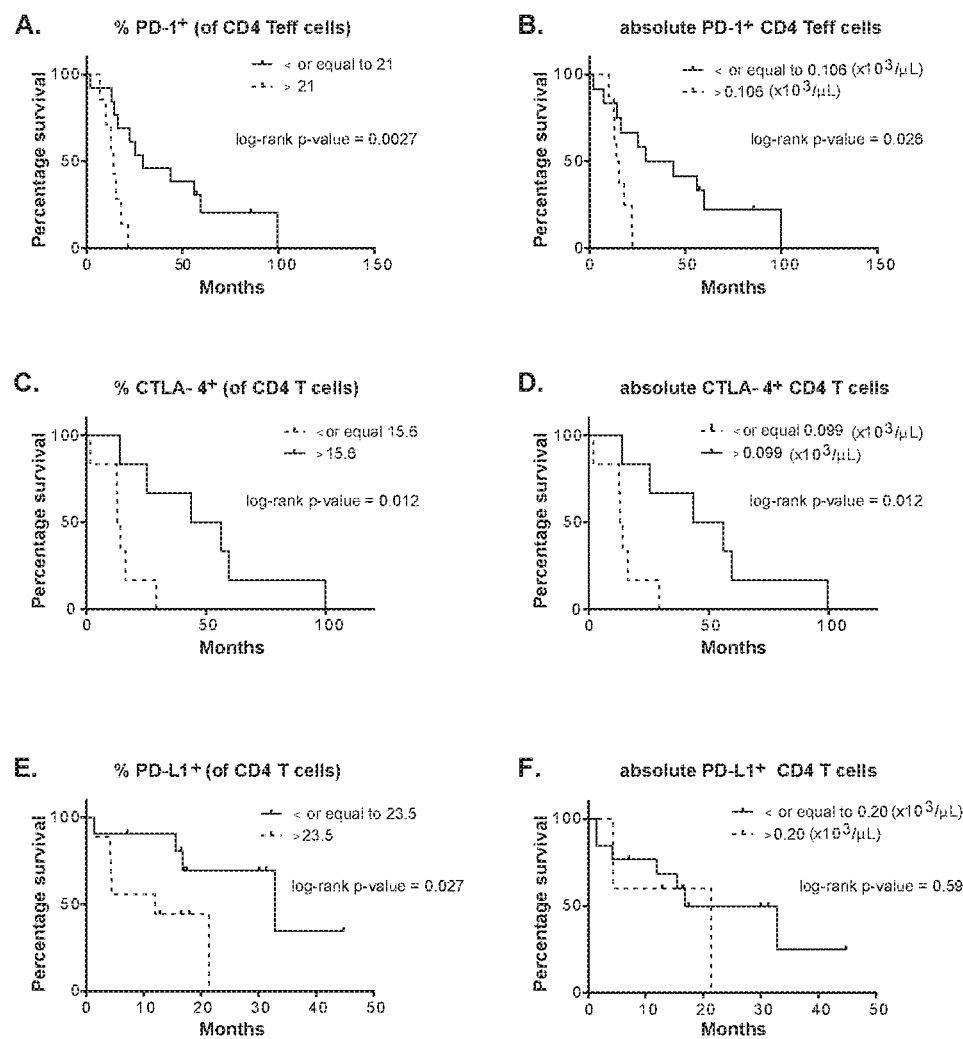
FIG. 10. Comparison of overall survival of patients separated by levels of immune subsets a designated in the legend. A and B, Kaplan-Meier plots of percentage of CD4 $T_{eff}$ cells that expressed PD-1 and absolute counts of PD-1$^+$ CD4 $T_{eff}$ cells respectively, separated by cutoff levels designated in the legend. C and D, Kaplan-Meier plots of percentage of CD4 T cells that expressed CTLA-4 and absolute counts of CTLA-4$^+$ CD4 T cells respectively, separated by cutoff levels designated in the legend. E and F, Kaplan-Meier plots of percentage of CD4 T cells that expressed PD-L1 and absolute counts of PD-L1$^+$ CD4 T cells respectively, separated by cutoff levels designated in the legend.

Establishing Optimal Cutoff Levels of Immune Subsets with Kaplan-Meier Plots and Log-Rank Test Overall survival of mCRPC patients with ≤21% of PD-1[+] of CD4 $T_{eff}$ cells was significantly different from overall survival of patients with >21% of PD-1[+] of CD4 $T_{eff}$ cells (p-value=0.0027, FIG. 10). Overall survival of mCRPC patients with ≤106 cells/µl of PD-1[+] CD4 $T_{eff}$ cells was significantly different from overall survival of patients with >106 cells/µl of PD-1[+] CD4 $T_{eff}$ cells (p-value=0.026, FIG. 10).

Overall survival of mCRPC patients with >15.6% of CTLA-4[+] of CD4 T cells was significantly different from overall survival of patients with ≤15.6% of CTLA-4[+] of CD4 T cells (p-value=0.012, FIG. 10). Overall survival of mCRPC patients with >99 cells/µl of CTLA-4[+] CD4 T cells was significantly different from overall survival of patients with ≤99 cells/µl of CTLA-4[+] CD4 T cells (p-value=0.012, FIG. 10).

Overall survival of metastatic melanoma patients with ≤23.5% of PD-L1[+] of CD4 T cells was significantly different from overall survival of patients with >23.5% of PD-L1[+] of CD4 T cells (p-value=0.027, FIG. 10).

Example 14

Intracellular Cytokine Expression of PD-1[+] CD4 $T_{eff}$ Cells

Cytokine expression patterns of PD-1[+] and PD-1[-]CD4 and CD8 T cells of pre-treatment PBMC from mCRPC patients were compared to PBMC from healthy donors (FIG. 11). Freshly thawed PBMC were stimulated with PMA and ionomycin for 4 hours in culture at 37° C., and intracellularly stained for IFNγ and IL-4. About 40% of PD-1[+]CD4 T cells expressed IFNγ compared to 5% of PD-1[-]CD4 T cells. On the other hand, almost 90% of PD-1[+]CD8 T cells expressed IFNγ, compared to 30 to 50% of PD-1[-]CD8 T cells. The ratio of PD-1[+]to PD-1[-] T cells expressing IFNγ is significantly greater for CD4 than for CD8 T cells. More PD-1[+] than PD-1[-]CD4 T cells expressed IL-4 although the levels were low. CD8 T cells did not express IL-4. The percentages of IFNγ and IL-4-expressing PD-1[+] and PD-1[-] CD4 T cells from cancer patients were comparable to healthy donors.

Unstimulated pre-treatment PBMC from mCRPC patients and unstimulated PBMC from healthy donors were also stained for surface CD49b and Lag-3, and for intracellular granzyme B (FIG. 11). More PD-1[+] CD4 T cells expressed CD49b, Lag-3, and granzyme B than PD-1[-] CD4 T cells. The percentages of Lag-3 expression were similar for cancer patients and healthy donors. However, the percentages of granzyme B and CD49b-expressing PD-1[+] CD4 T cells were higher in cancer patients than in healthy donors. Granzyme B-expressing PD-1[-] CD4 T cells were also greater in cancer patients than in healthy donors, whereas CD49b-expressing PD-1[-] CD4 were similar for cancer patients and healthy donors. CD8 T cells displayed a different pattern of expression of granzyme B compared to CD4 T cells. Similar percentages of PD-1[+] and PD-1[-] CD8 T cells from cancer patients expressed granzyme B, and both levels were higher than those from healthy donors. More PD-1[+] than PD-1[-] CD8 T cells from healthy donors expressed granzyme B. Expressions of Lag-3 and CD49b were low and did not differ for PD-1[+] and PD-1[-] CD8 T cells, or for cancer patients and healthy donors.

Each of the references cited below is incorporated by reference herein in its entirety, or in relevant part, as would be apparent from context. The references are cited throughout this disclosure using superscripted numbers corresponding to the following numbered reference list.

REFERENCES

1. Walunas T L, Lenschow D J, Bakker C Y, Linsley P S, Freeman G J, Green J M, et al. CTLA-4 can function as a negative regulator of T cell activation. Immunity 1994; 1:405-13.
2. Krummel M F, Allison J P. CD28 and CTLA-4 have opposing effects on the response of T cells to stimulation. The Journal of experimental medicine 1995; 182:459-65.
3. Hodi F S, O'Day S J, McDermott D F, Weber R W, Sosman J A, Haanen J B, et al. Improved survival with ipilimumab in patients with metastatic melanoma. The New England journal of medicine 2010; 363:711-23.
4. Robert C, Thomas L, Bondarenko I, O'Day S, M D J, Garbe C, et al. Ipilimumab plus dacarbazine for previously untreated metastatic melanoma. The New England journal of medicine 2011; 364:2517-26.
5. Prieto P A, Yang J C, Sherry R M, Hughes M S, Kammula U S, White D E, et al. CTLA-4 blockade with ipilimumab: long-term follow-up of 177 patients with metastatic melanoma. Clinical cancer research: an official journal of the American Association for Cancer Research 2012; 18:2039-47.
6. McDermott D, Lebbe C, Hodi F S, Maio M, Weber J S, Wolchok J D, et al. Durable benefit and the potential for long-term survival with immunotherapy in advanced melanoma. Cancer treatment reviews 2014.

7. Hodi F S, Lee S, McDermott D F, Rao U N, Butterfield L H, Tarhini A A, et al. Ipilimumab plus sargramostim vs ipilimumab alone for treatment of metastatic melanoma: a randomized clinical trial. JAMA: the journal of the American Medical Association 2014; 312:1744-53.
8. Kwon E D, Drake C G, Scher H I, Fizazi K, Bossi A, van den Eertwegh A J, et al. Ipilimumab versus placebo after radiotherapy in patients with metastatic castration-resistant prostate cancer that had progressed after docetaxel chemotherapy (CA184-043): a multicentre, randomised, double-blind, phase 3 trial. The lancet oncology 2014; 15:700-12.
9. Ku G Y, Yuan J, Page D B, Schroeder S E, Panageas K S, Carvajal R D, et al. Single-institution experience with ipilimumab in advanced melanoma patients in the compassionate use setting: lymphocyte count after 2 doses correlates with survival. Cancer 2010; 116:1767-75.
10. Wolchok J D, Kluger H, Callahan M K, Postow M A, Rizvi N A, Lesokhin A M, et al. Nivolumab plus ipilimumab in advanced melanoma. The New England journal of medicine 2013; 369:122-33.
11. Hoos A. Endpoints for Immunotherapy Studies: Design and Regulatory Implications; Proposal of a Clinical Development Paradigm for Cancer Immunotherapy. 2008.

The disclosed subject matter has been described with reference to various specific and preferred embodiments and techniques. It should be understood, however, that many variations and modifications may be made while remaining within the spirit and scope of the disclosed subject matter.

What is claimed is:

1. A method of treating cancer in a human subject having cancer by determining if the subject is amenable to treatment with ipilimumab and administering to the subject determined to be amenable to treatment with ipilimumab an effective amount of ipilimumab to treat the cancer in the subject, said method comprising:
    (a) isolating a population of peripheral blood mononuclear cells (PBMCs) from the subject having cancer and a population of PBMCs from a cancer-free human subject;
    (b) quantifying the percentages of $CD4^+CD3^+$ $FoxP3^-$ T effector ($T_{eff}$) cells expressing PD1, PD-L1, and/or CTLA-4 in each of said populations;
    (c) comparing the percentages of $T_{eff}$ cells expressing PD1, PD-L1, and/or CTLA-4 in the population of PBMCs from the subject having cancer and the percentages of $T_{eff}$ cells expressing PD1, PD-L1, and/or CTLA-4 in the population of PBMCs from the cancer-free subject;
    (d) determining that the subject having cancer is amenable to treatment with ipilimumab if:
        (1) the percentage of $T_{eff}$ cells expressing PD-1 in the population of PBMCs from the subject having cancer is lower than the percentage of $T_{eff}$ cells expressing PD-1 in the population of PBMCs from the cancer-free subject;
        (2) the percentage of $T_{eff}$ cells expressing PD-L1 in the population of PBMCs from the subject having cancer is lower than the percentage of $T_{eff}$ cells expressing PD-L1 in the population of PBMCs from the cancer-free subject; and
        (3) the percentage of $T_{eff}$ cells expressing CTLA-4 in the population of PBMCs from the subject having cancer is higher than the percentage of $T_{eff}$ cells expressing CTLA-4 in the population of PBMCs from the cancer-free subject; and
    (e) if the subject having cancer is determined to be amenable to treatment with ipilimumab, administering to the subject an effective amount of ipilimumab to treat the cancer in the subject.

2. The method of claim 1, wherein the cancer is an adenocarcinoma, a castration-resistant prostate cancer, a melanoma, a Head-and-Neck cancer, a lung cancer, a kidney cancer, a bladder cancer, a gastric cancer, a colorectal cancer, an ovarian cancer, a hepatocellular cancer, a hepatobiliary cancer, a breast cancer, or a blood cancer.

3. A method of inhibiting growth of cancer in a human subject having cancer by determining if the subject is amenable to treatment with ipilimumab and administering to the subject determined to be amenable to treatment with ipilimumab an effective amount of ipilimumab to inhibit growth of the cancer in the subject, said method comprising:
    (a) isolating a population of peripheral blood mononuclear cells (PBMCs) from the subject having cancer and a population of PBMCs from a cancer-free human subject;
    (b) quantifying the percentages of $CD4^+CD3^+$ $FoxP3^-$ T effector ($T_{eff}$) cells expressing PD1, PD-L1, and/or CTLA-4 in each of said populations;
    (c) comparing the percentages of $T_{eff}$ cells expressing PD1, PD-L1, and/or CTLA-4 in the population of PBMCs from the subject having cancer and the percentages of $T_{eff}$ cells expressing PD1, PD-L1, and/or CTLA-4 in the population of PBMCs from the cancer-free subject;
    (d) determining that the subject having cancer is amenable to treatment with ipilimumab if:
        (1) the percentage of $T_{eff}$ cells expressing PD-1 in the population of PBMCs from the subject having cancer is lower than the percentage of $T_{eff}$ cells expressing PD-1 in the population of PBMCs from the cancer-free subject;
        (2) the percentage of $T_{eff}$ cells expressing PD-L1 in the population of PBMCs from the subject having cancer is lower than the percentage of $T_{eff}$ cells expressing PD-L1 in the population of PBMCs from the cancer-free subject; and
        (3) the percentage of $T_{eff}$ cells expressing CTLA-4 in the population of PBMCs from the subject having cancer is higher than the percentage of $T_{eff}$ cells expressing CTLA-4 in the population of PBMCs from the cancer-free subject; and
    (e) if the subject having cancer is determined to be amenable to treatment with ipilimumab, administering to the subject an effective amount of ipilimumab to inhibit growth of the cancer in the subject.

4. The method of claim 3, wherein the cancer is an adenocarcinoma, a castration-resistant prostate cancer, a melanoma, a Head-and-Neck cancer, a lung cancer, a kidney cancer, a bladder cancer, a gastric cancer, a colorectal cancer, an ovarian cancer, a hepatocellular cancer, a hepatobiliary cancer, a breast cancer, or a blood cancer.

5. A method of treating cancer in a human subject having cancer by determining if the subject is amenable to treatment with ipilimumab and administering to the subject determined to be amenable to treatment with ipilimumab an effective amount of ipilimumab to treat the cancer in the subject, said method comprising:
    (a) isolating a population of peripheral blood mononuclear cells (PBMCs) from the subject having cancer and a population of PBMCs from a cancer-free human subject;

(b) quantifying the percentages of total CD4$^+$ cells expressing PD1, PD-L1, and/or CTLA-4 in each of said populations;
(c) comparing the percentages of total CD4$^+$ cells expressing PD1, PD-L1, and/or CTLA-4 in the population of PBMCs from the subject having cancer and the percentages of total CD4$^+$ cells expressing PD1, PD-L1, and/or CTLA-4 in the population of PBMCs from the cancer-free subject;
(d) determining that the subject having cancer is amenable to treatment with ipilimumab if:
 (1) the percentage of total CD4$^+$ cells expressing PD-1 in the population of PBMCs from the subject having cancer is lower than the percentage of total CD4$^+$ cells expressing PD-1 in the population of PBMCs from the cancer-free subject;
 (2) the percentage of total CD4$^+$ cells expressing PD-L1 in the population of PBMCs from the subject having cancer is lower than the percentage of total CD4$^+$ cells expressing PD-L1 in the population of PBMCs from the cancer-free subject; and
 (3) the percentage of total CD4$^+$ cells expressing CTLA-4 in the population of PBMCs from the subject having cancer is higher than the percentage of total CD4$^+$ cells expressing CTLA-4 in the population of PBMCs from the cancer-free subject; and
(e) if the subject having cancer is determined to be amenable to treatment with ipilimumab, administering to the subject an effective amount of ipilimumab to treat the cancer in the subject.

6. The method of claim 3, wherein the cancer is an adenocarcinoma, a castration-resistant prostate cancer, a melanoma, a Head-and-Neck cancer, a lung cancer, a kidney cancer, a bladder cancer, a gastric cancer, a colorectal cancer, an ovarian cancer, a hepatocellular cancer, a hepatobiliary cancer, a breast cancer, or a blood cancer.

* * * * *